US012662937B2

(12) United States Patent
El Mallawany et al.

(10) Patent No.: US 12,662,937 B2
(45) Date of Patent: *Jun. 23, 2026

(54) SENSOR FOR QUANTIFYING PRODUCTION FLUID PERCENTAGE CONTENT

(71) Applicant: Halliburton Energy Services, Inc., Houston, TX (US)

(72) Inventors: Ibrahim El Mallawany, Al-Khobar (SA); Michael Linley Fripp, Singapore (SG); Stephen Michael Greci, Carrollton, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/990,198

(22) Filed: Dec. 20, 2024

(65) Prior Publication Data

US 2025/0122800 A1     Apr. 17, 2025

Related U.S. Application Data

(63) Continuation of application No. 17/878,600, filed on Aug. 1, 2022, now Pat. No. 12,196,077.

(51) Int. Cl.
E21B 49/08          (2006.01)
E21B 47/12          (2012.01)
(Continued)

(52) U.S. Cl.
CPC .............. E21B 49/08 (2013.01); E21B 47/12 (2013.01); G01N 9/12 (2013.01); G01N 33/2823 (2013.01);
(Continued)

(58) Field of Classification Search
None
See application file for complete search history.

(56) References Cited

U.S. PATENT DOCUMENTS 1,155,733 A     10/1915  Jack
3,631,727 A      1/1972  White
(Continued)

FOREIGN PATENT DOCUMENTS

EP          1298427 A1     4/2003
WO          9105135 A1     4/1991

*Primary Examiner* — Blake Michener
(74) *Attorney, Agent, or Firm* — Scott Richardson; Parker Justiss, P.C.

(57) ABSTRACT

Provided is a downhole tool and a well system. The downhole tool, in one aspect, includes a tubular providing one or more production fluid flow paths for a production fluid. The downhole tool, according to this aspect, further includes one or more float chambers located within the tubular, and two or more floats located within the one or more float chambers. In one aspect, a first of the two or more floats has a first density ($\rho_1$) between a density of gas ($\rho_g$) and a density of oil ($\rho_o$), and a second of the two or more floats has a second density ($\rho_2$) between the density of oil ($\rho_o$) and a density of water ($\rho_w$). The downhole tool, according to this aspect, further includes two or more non-contact proximity sensors configured to sense a radial location of the two or more floats to determine a gas:oil ratio and oil:water ratio.

42 Claims, 26 Drawing Sheets

(51) Int. Cl.
    *G01N 9/12*         (2006.01)
    *G01N 33/28*       (2006.01)

(52) U.S. Cl.
    CPC ..... *G01N 33/2841* (2013.01); *G01N 33/2847*
                              (2013.01)

(56)           References Cited

U.S. PATENT DOCUMENTS

| | | | |
|---|---|---|---|
| 3,678,760 A | 7/1972 | Bonnet | |
| 4,702,109 A | 10/1987 | Viola | |
| 4,905,508 A | 3/1990 | LaRette | |
| 5,045,692 A | 9/1991 | Arnold | |
| 5,950,487 A | 9/1999 | Maresca, Jr. et al. | |
| 6,502,461 B2* | 1/2003 | Keller | G01F 23/72 |
| | | | 73/309 |
| 6,928,862 B1* | 8/2005 | Robbins | G01F 23/14 |
| | | | 73/299 |
| 7,278,293 B2* | 10/2007 | Sierra | G01N 33/28 |
| | | | 73/309 |
| 7,730,779 B2* | 6/2010 | Mahadevaiah | G01F 23/76 |
| | | | 73/291 |
| 8,286,483 B2 | 10/2012 | Mahadevaiah | |
| 8,539,828 B2* | 9/2013 | Prinstil | G01N 9/14 |
| | | | 73/305 |
| 8,754,374 B1 | 6/2014 | Hewitson | |
| 8,878,682 B2 | 11/2014 | Kenney et al. | |
| 10,794,865 B2 | 10/2020 | Sinha et al. | |
| 11,041,361 B2 | 6/2021 | Fripp et al. | |
| 11,231,339 B2 | 1/2022 | Buckley et al. | |
| 11,555,733 B2 | 1/2023 | Beckett | |
| 11,892,336 B2* | 2/2024 | Beckett | G01N 9/10 |
| 2008/0223130 A1 | 9/2008 | Snell et al. | |
| 2011/0185794 A1 | 8/2011 | Moss | |
| 2016/0047228 A1 | 2/2016 | Frosell et al. | |
| 2016/0168977 A1 | 6/2016 | Donderici et al. | |
| 2020/0064871 A1 | 2/2020 | Fripp et al. | |
| 2020/0291745 A1 | 9/2020 | Greci et al. | |
| 2020/0308927 A1 | 10/2020 | Fripp et al. | |
| 2023/0160871 A1 | 5/2023 | Hunsley et al. | |
| 2024/0035372 A1 | 2/2024 | El Mallawany et al. | |

* cited by examiner

200

210

240

250

SENSOR FOR QUANTIFYING PRODUCTION FLUID PERCENTAGE CONTENT

CROSS-REFERENCE TO RELATED APPLICATION

This application is a continuation of application Ser. No. 17/878,600, filed on Aug. 1, 2022, entitled "SENSOR FOR QUANTIFYING PRODUCTION FLUID PERCENTAGE CONTENT," commonly assigned with the present application are incorporated herein by reference as if reproduced herein in its entirety.

BACKGROUND

Wellbores are sometimes drilled from the surface of a wellsite several hundred to several thousand feet downhole to reach hydrocarbon resources. During certain well operations, such as production operations, certain fluids, such as fluids of hydrocarbon resources, are extracted from the formation. For example, the fluids of hydrocarbon resources may flow into one or more sections of a conveyance such as a section of a tubing (e.g., production tubing), and through the tubing, uphole to the surface. During production operations, other types of fluids, such as water, sometimes also flow into the section of production tubing while the fluids of hydrocarbon resources are being extracted.

BRIEF DESCRIPTION

Reference is now made to the following descriptions taken in conjunction with the accompanying drawings, in which.

Figure 8A:
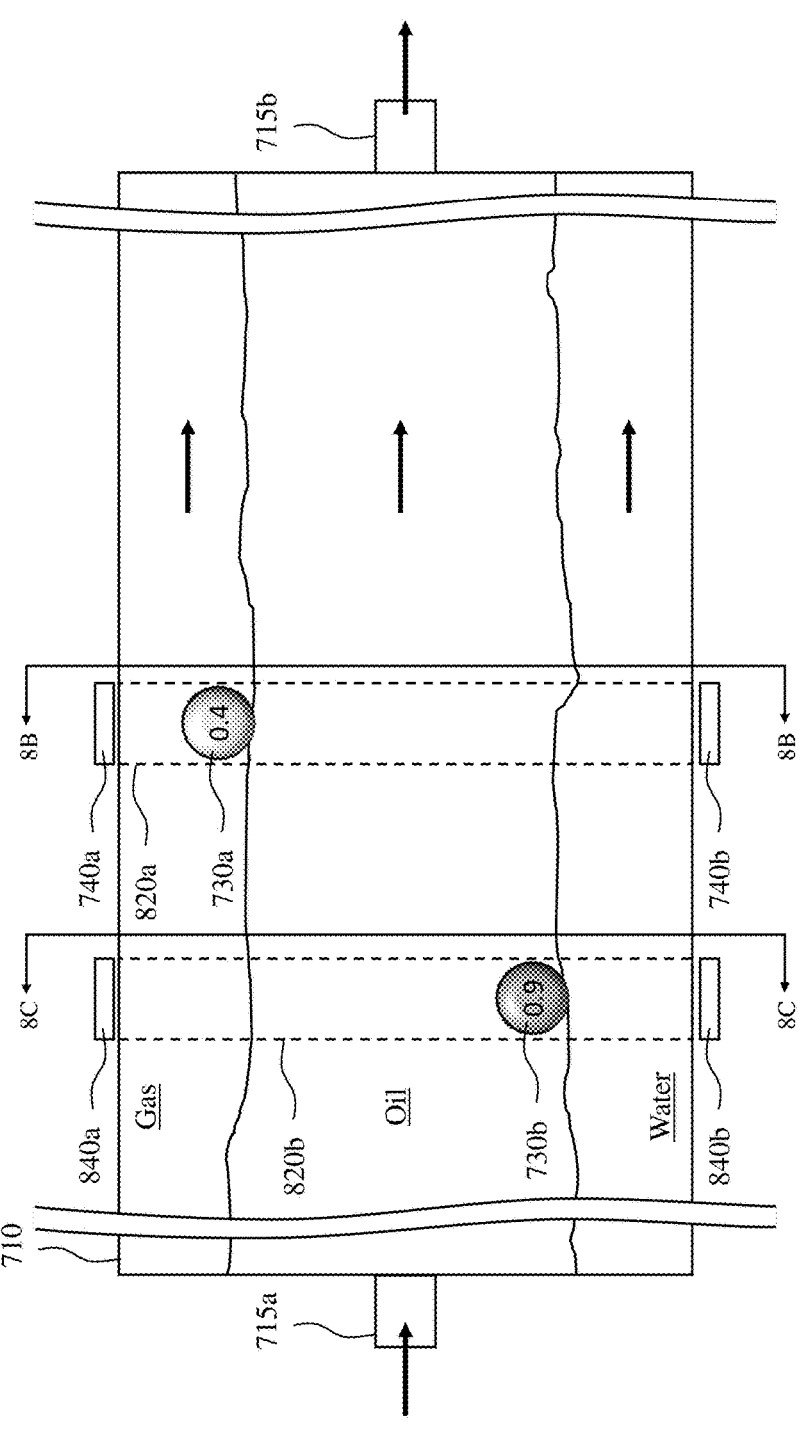
Figure 8B:
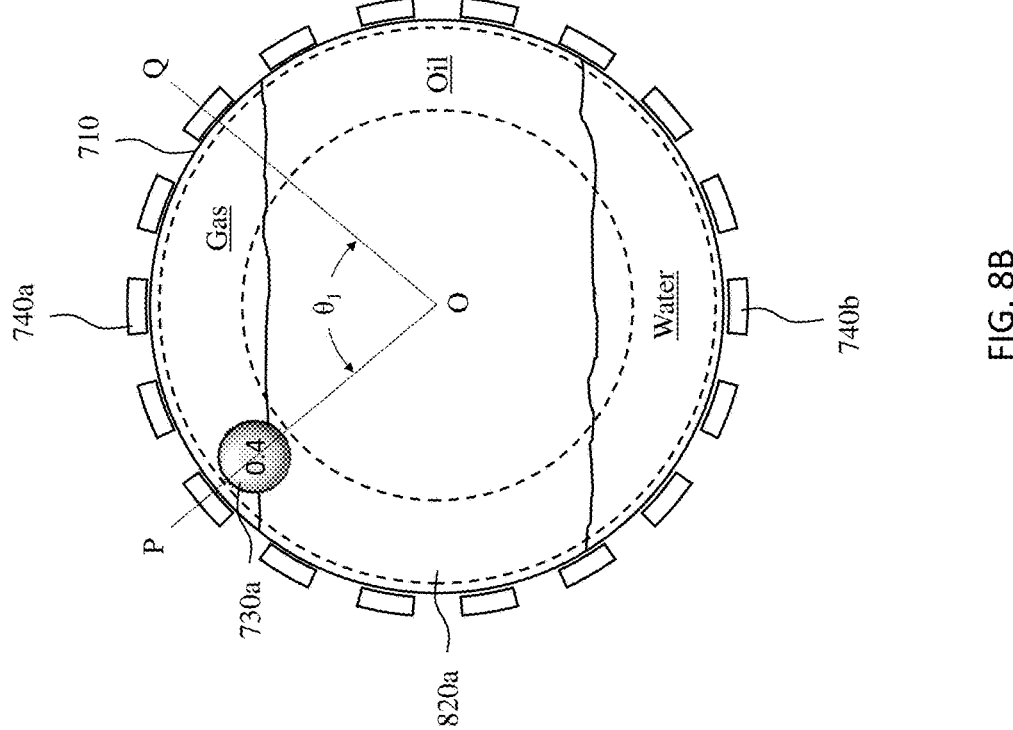
Figure 8B:
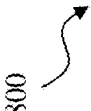
Figure 8C:
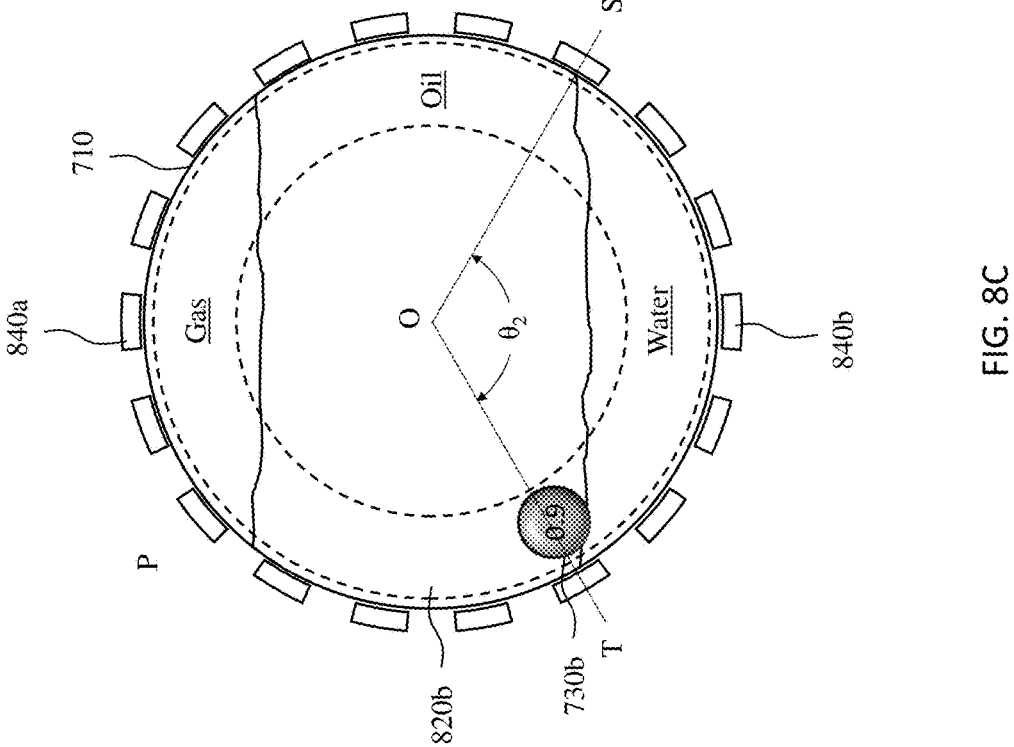
Figure 8C:
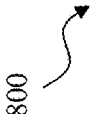
Figure 9A:
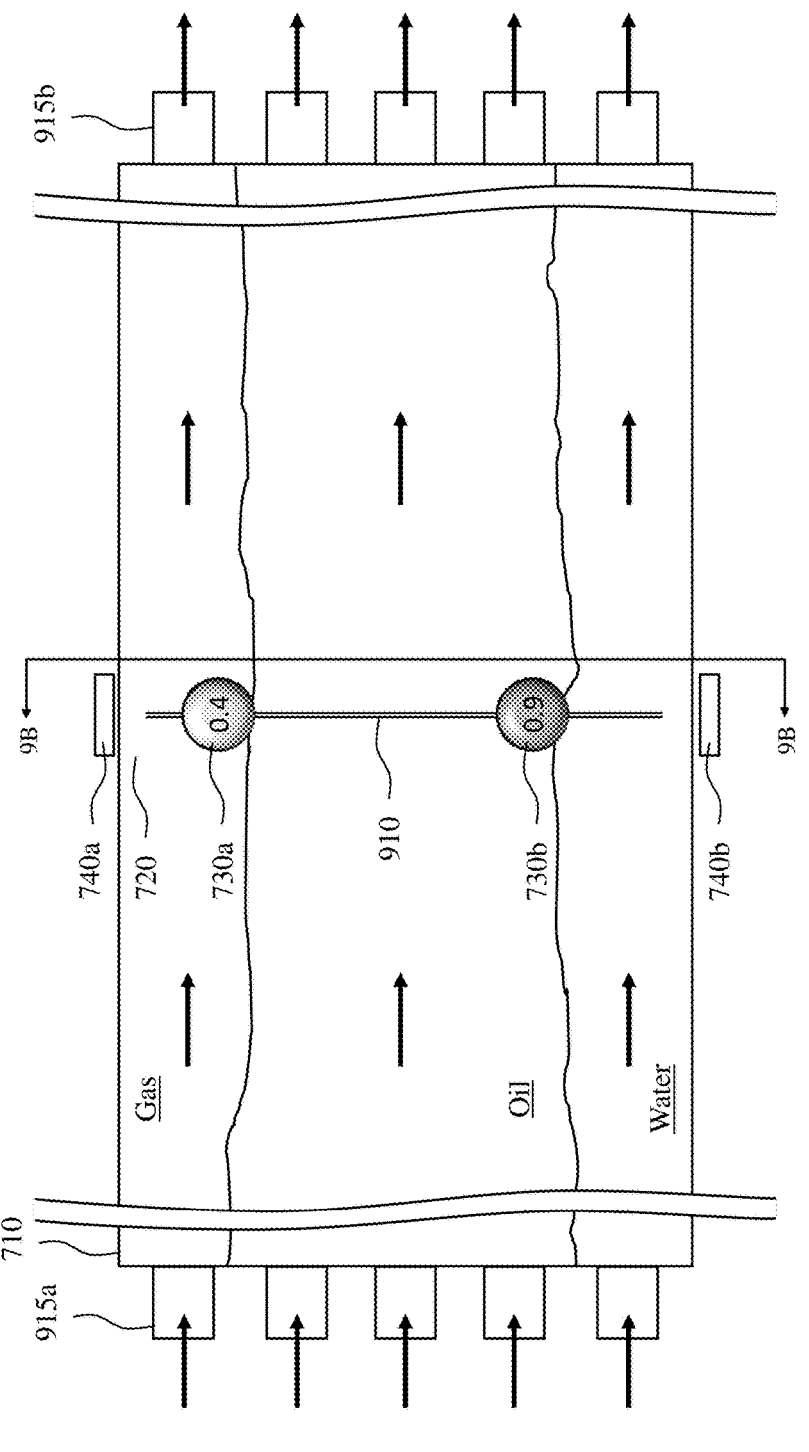
Figure 9B:
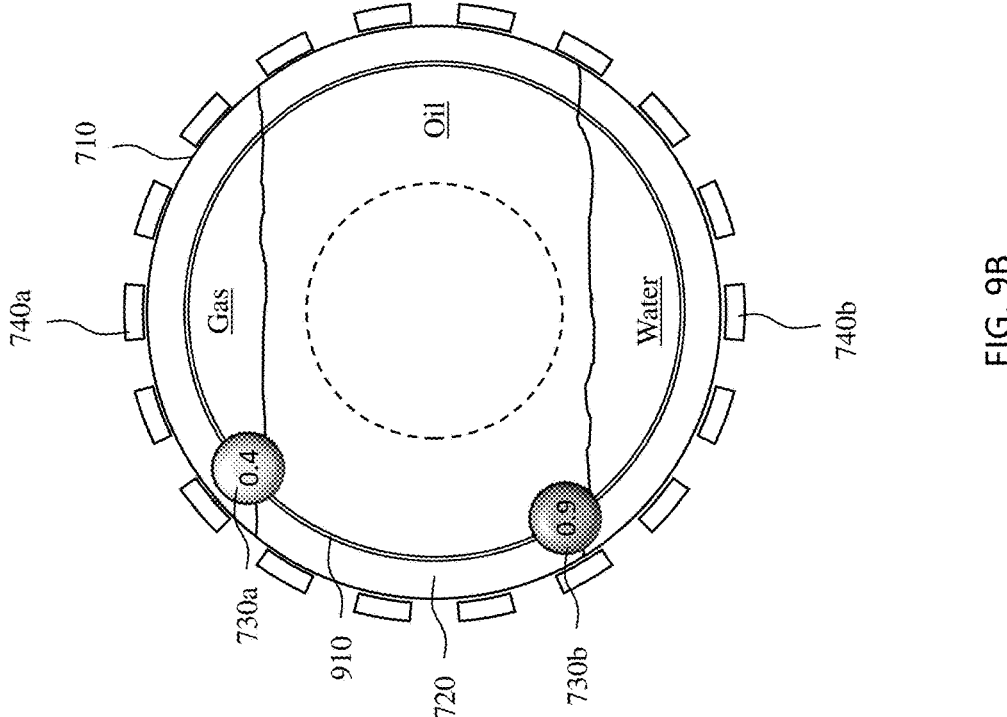
Figure 9B:
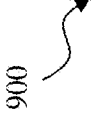
Figure 10A:
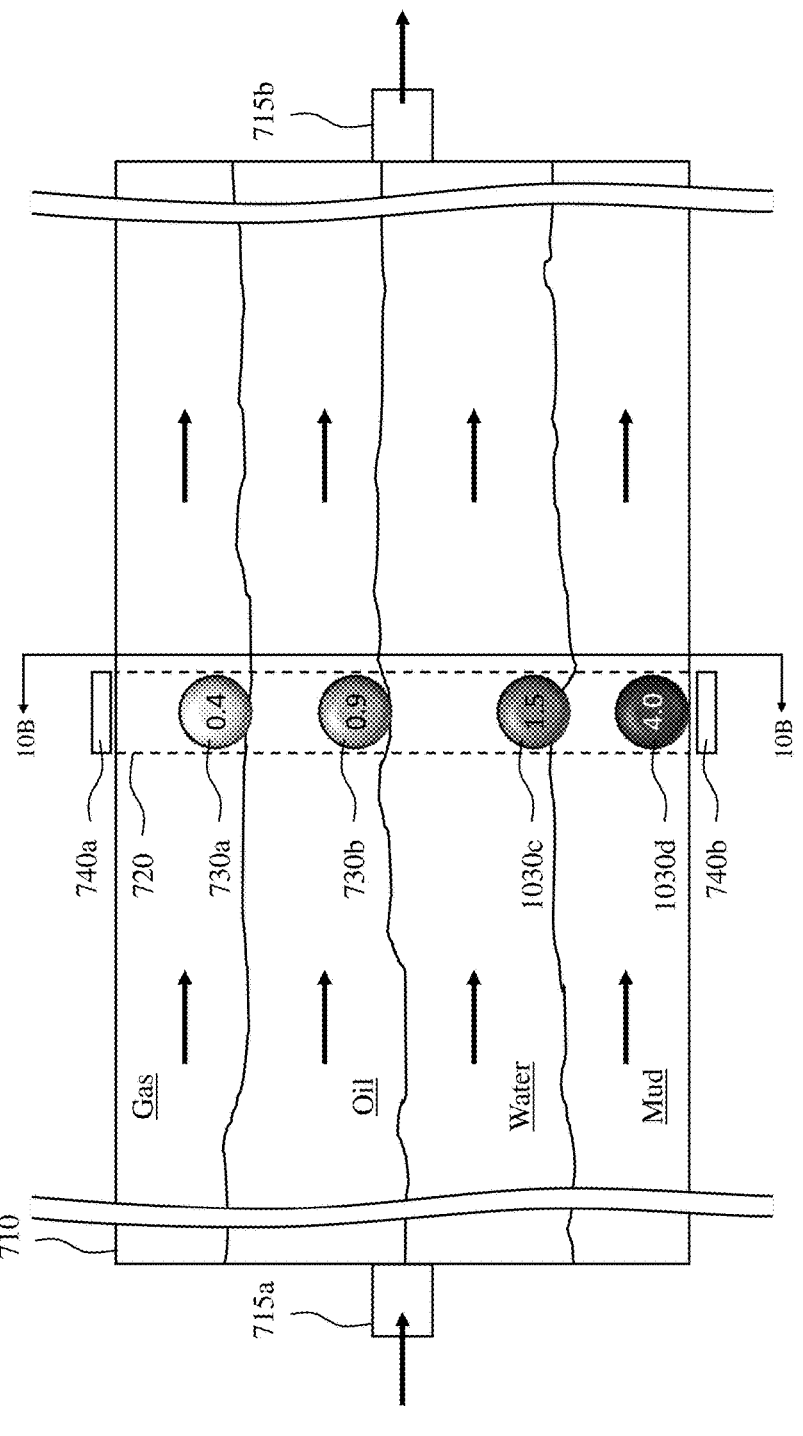
Figure 10B:
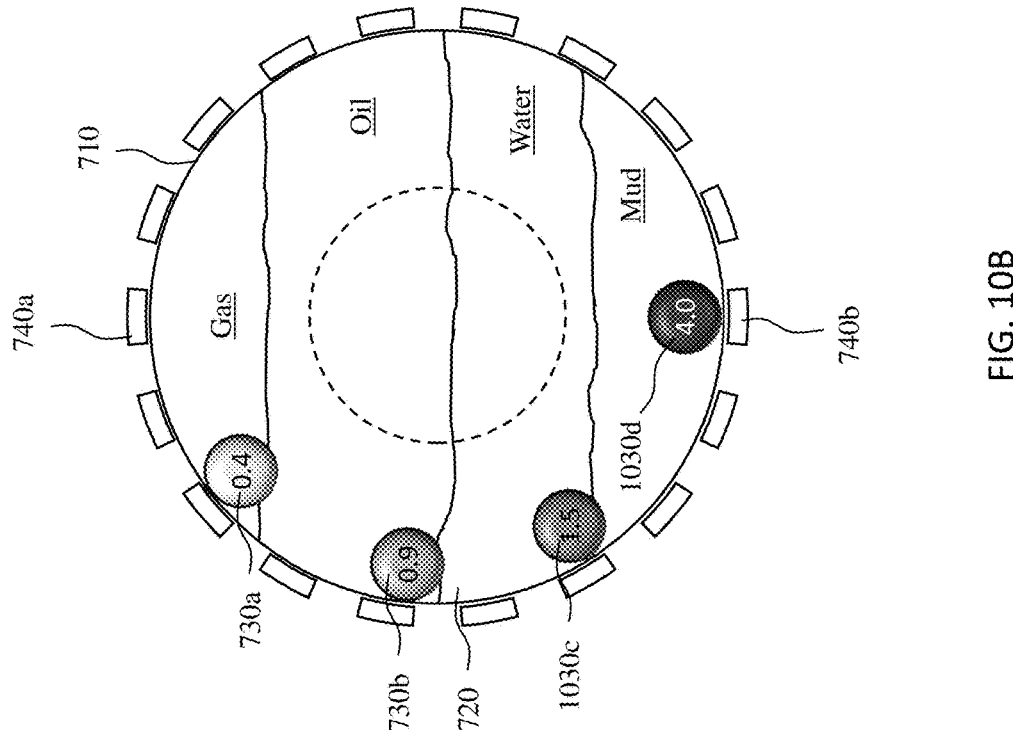
Figure 10B:
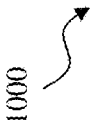

FIGS. 8A through 8C illustrated various different views of a downhole tool designed, manufactured and/or operated according to one or more alternative embodiments of the disclosure;

FIGS. 9A and 9B illustrate various different views of a downhole tool designed, manufactured and/or operated according to one or more alternative embodiments of the disclosure; and FIGS. 10A and 10B illustrate various different views of a downhole tool designed, manufactured and/or operated according to one or more alternative embodiments of the disclosure.

DETAILED DESCRIPTION

In the drawings and descriptions that follow, like parts are typically marked throughout the specification and drawings with the same reference numerals, respectively. The drawn figures are not necessarily to scale. Certain features of the disclosure may be shown exaggerated in scale or in somewhat schematic form and some details of certain elements may not be shown in the interest of clarity and conciseness. The present disclosure may be implemented in embodiments of different forms.

Specific embodiments are described in detail and are shown in the drawings, with the understanding that the present disclosure is to be considered an exemplification of the principles of the disclosure, and is not intended to limit the disclosure to that illustrated and described herein. It is to be fully recognized that the different teachings of the embodiments discussed herein may be employed separately or in any suitable combination to produce desired results.

Unless otherwise specified, use of the terms "connect," "engage," "couple," "attach," or any other like term describing an interaction between elements is not meant to limit the interaction to direct interaction between the elements and may also include indirect interaction between the elements described. Unless otherwise specified, use of the terms "up," "upper," "upward," "uphole," "upstream," or other like terms shall be construed as generally away from the bottom, terminal end of a well, regardless of the wellbore orientation; likewise, use of the terms "down," "lower," "downward," "downhole," or other like terms shall be construed as generally toward the bottom, terminal end of a well, regardless of the wellbore orientation. Use of any one or more of the foregoing terms shall not be construed as denoting positions along a perfectly vertical axis. In some instances, a part near the end of the well can be horizontal or even slightly directed upwards. Unless otherwise specified, use of the term "subterranean formation" shall be construed as encompassing both areas below exposed earth and areas below earth covered by water such as ocean or fresh water.

The present disclosure relates, for the most part, to a density sensor and downhole tool including the same. The density sensor, in at least one embodiment, includes one or more float chambers, as well as two or more floats located within the one or more float chambers. In accordance with one embodiment, the two or more floats have a density ranging from 0.08 sg to 2.1 sg. For example, the two or more floats could have a density ranging from one of the less dense materials within a wellbore (e.g., gas) and one of the more dense materials within a wellbore (e.g., mud). Density values for the two or more floats far outside of this range would not provide as useful information as density values within this range. Further to this embodiment, a first of the two or more floats has a first known density ($\rho_1$) and a second of the two or more floats has a second known density ($\rho_2$) greater than the first known density ($\rho_1$). The density sensor, according to this embodiment, may further include one or more sensors located proximate the one or more float chambers. In accordance with this embodiment, the one or more sensors are configured to sense whether ones of the two or more floats sink or float within production fluid having an unknown density $(\rho_f)$. Accordingly, the two or more floats having known densities, as well as the one or more sensors, may be used (e.g., along with related electronics) to calculate an approximation for the unknown density $(\rho_f)$ of the production fluid (e.g., based upon sensed values of whether ones of the two or more floats sink or float within the production fluid).

Figure 1:
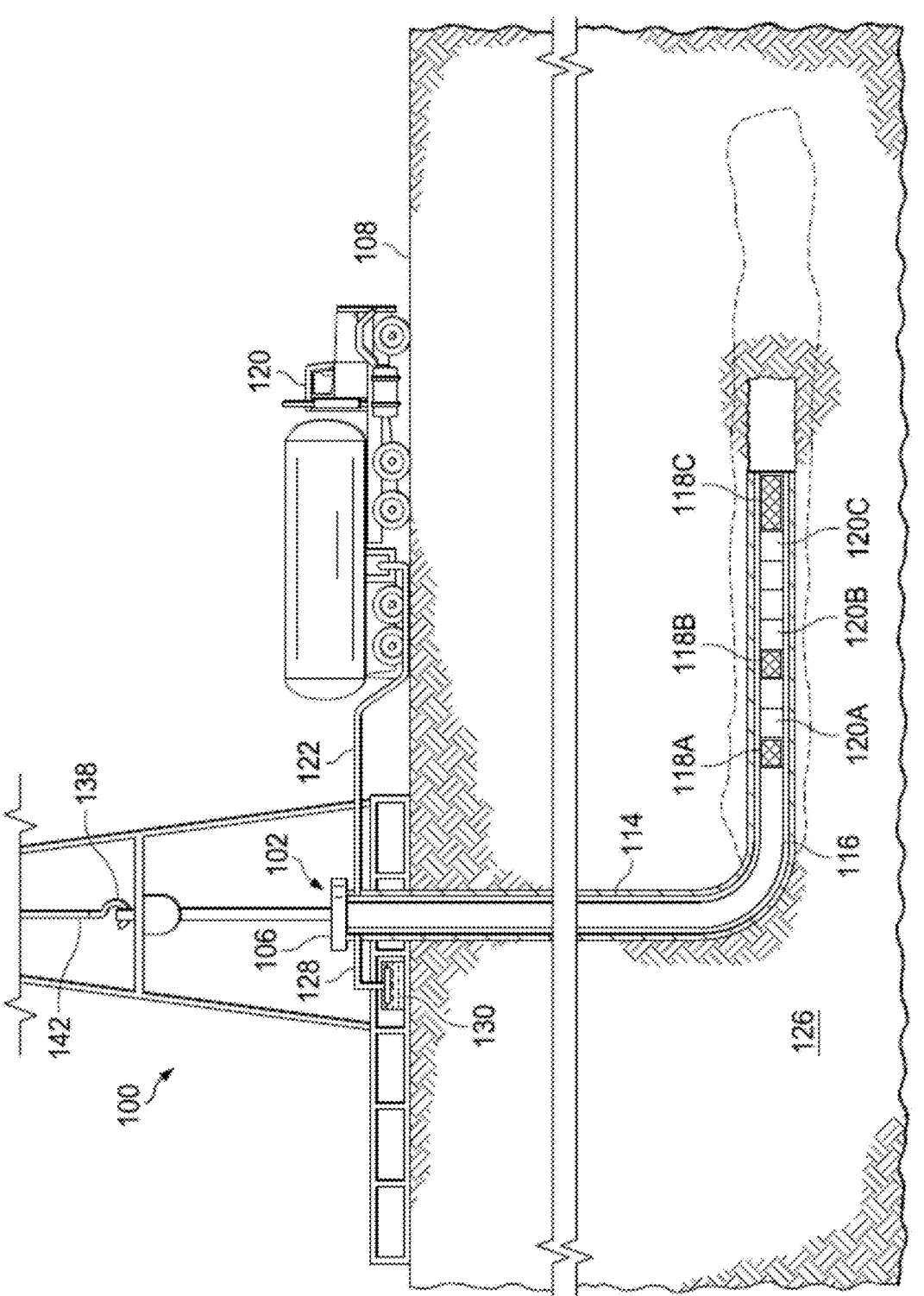
FIG. 1 illustrates a schematic, side view of a well system in which density sensors designed, manufactured and/or operated according to the present disclosure are deployed in a wellbore.

Turning now to the figures, FIG. 1 illustrates a schematic, side view of a well system 100 in which density sensors 120A-120C designed, manufactured and/or operated according to the present disclosure are deployed in a wellbore 114. As shown in FIG. 1, wellbore 114 extends from surface 108 of well 102 to or through one or more formations 126. A hook 138, a cable 142, traveling block (not shown), and hoist (not shown) may be provided to lower conveyance 116 into well 102. As referred to herein, conveyance 116 is any piping, tubular, or fluid conduit including, but not limited to, drill pipe, tubing (e.g., production tubing), casing, coiled tubing, and any combination thereof. Conveyance 116 provides a conduit for fluids extracted from formation 126 to travel to surface 108. In some embodiments, conveyance 116 additionally provides a conduit for fluids to be conveyed downhole and injected into formation 126, such as in an injection operation. In some embodiments, conveyance 116 is coupled to a production tubing that is arranged within a horizontal section of well 102. In the embodiment of FIG. 1, conveyance 116 and the production tubing are represented by the same tubing.

At wellhead 106, an inlet conduit 122 is coupled to a fluid source 120 to provide fluids through conveyance 116 downhole. For example, drilling fluids, fracturing fluids, and injection fluids are pumped downhole during drilling operations, hydraulic fracturing operations, and injection operations, respectively. In the embodiment of FIG. 1, fluids are circulated into well 102 through conveyance 116 and back toward surface 108. To that end, a diverter or an outlet conduit 128 may be connected to a container 130 at the wellhead 106 to provide a fluid return flow path from wellbore 114. Conveyance 116 and outlet conduit 128 also form fluid passageways for fluids, such as hydrocarbon resources to flow uphole during production operations.

In the embodiment of FIG. 1, conveyance 116 includes production tubular sections 118A-118C at different production intervals adjacent to formation 126. In some embodiments, packers (now shown) are positioned on the left and right sides of production tubular sections 118A-118C to define production intervals and provide fluid seals between the respective production tubular section 118A, 118B, or 118C, and the wall of wellbore 114. Production tubular sections 118A-118C, in the embodiment of FIG. 1 include density sensors 120A-120C positioned at the different production intervals, and designed, manufactured and/or operated according to one or more embodiments of the present disclosure. The density sensors 120A-120C are configured to provide an approximation for the unknown density $(\rho_f)$ of the production fluid entering each the production tubular sections 118A-118C, which heretofore was unavailable.

The respective production tubular sections 118A-118C, may further include one or more wellbore screens and one or more inflow control devices (ICDs). An inflow control device controls the volume or composition of the fluid flowing from a production interval through the wellbore screens and into a production tubular section, e.g., 118A-118C. For example, a production interval defined by the respective production tubular sections 118A-118C may produce more than one type of fluid component, such as a mixture of oil, water, steam, carbon dioxide, and natural gas. Inflow control devices, which are fluidly coupled to production tubular sections 118A-118C, may reduce or restrict the flow of fluid into the respective production tubular sections 118A-118C when the production interval is producing a higher proportion of an undesirable fluid component, such as water This permits the other production intervals that are producing a higher proportion of a desired fluid component (e.g., oil) to contribute more to the production fluid at surface 108 of well 102, so that the production fluid has a higher proportion of the desired fluid component. In some embodiments, inflow control devices are an autonomous inflow control devices (AICD) that permits or restricts fluid flow into the production tubular sections 118A-118C based on fluid density, without requiring signals from the well's surface by the well operator. In at least one embodiment, the density sensors 120A-120C provide feedback control of the inflow control devices.

Figure 2:
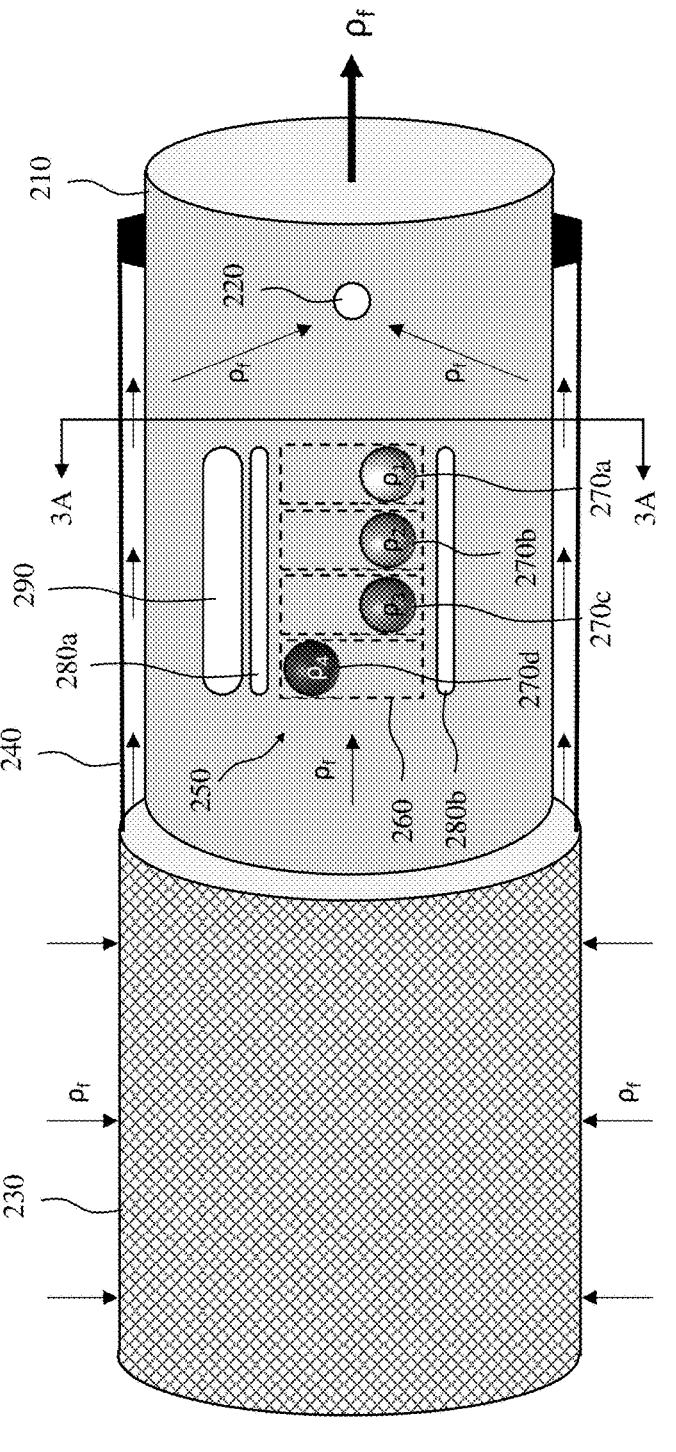
FIG. 2 illustrates a cross-sectional view of one embodiment of a downhole tool designed, manufactured and/or operated according to one or more embodiments of the disclosure.

FIG. 2 illustrates a cross-sectional view of one embodiment of a downhole tool 200 designed, manufactured and/or operated according to one or more embodiments of the disclosure. The downhole tool 200, in at least one embodiment, includes a tubular 210 (e.g., production tubing) providing one or more production fluid flow paths (e.g., as shown by the arrows) for production fluid (e.g., having an unknown density $(\rho_f)$) to travel from a production interval of a subterranean formation through an inflow control device 220 and uphole to a surface of the wellbore. The inflow control device 220 may comprise a flow restrictor, such as a fixed flow restrictor (e.g., as shown), or can alternatively be a variable restrictor, such as an interval control valve (ICV) or autonomous interval control device (AICD). The downhole tool 200, in the illustrated embodiment, further includes a wellbore screen 230 positioned radially about the tubular 210. In the illustrated embodiment, the wellbore screen 230 is configured to receive the production fluid having the unknown density $(\rho_f)$ and provide it to an annulus defined between an outer surface of the tubular 210 and a radial outer housing 240.

The downhole tool 200, in the illustrated embodiment, further includes a density sensor 250 positioned within the one or more production fluid paths. In the illustrated embodiment of FIG. 2, the density sensor 250 is positioned in an annulus defined between the outer surface of the tubular 210 and the radial outer housing 240. While not shown in the embodiment of FIG. 2, the density sensor 250 could also be positioned within an interior surface of the tubular 210, or alternatively within a sidewall of the tubular 210.

The density sensor 250, in accordance with one embodiment, may include one or more float chambers 260. While a plurality of float chambers 260 (e.g., four float chambers) are illustrated in the embodiment of FIG. 2, other embodiments may exist wherein a single float chamber is used, or two or more float chambers are used. The one or more float chambers 260, in at least one embodiment, comprise one or more cages and/or enclosures that allow the production fluid having the unknown density $(\rho_f)$ to pass (e.g., easily pass) therethrough.

The density sensor 250, in accordance with at least one embodiment, further includes two or more floats 270 located within the one or more float chambers 260. In accordance with one embodiment of the disclosure, the two or more floats 270 have a density ranging from 0.08 sg to 2.1 sg. Furthermore, in at least one embodiment, a first 270a of the two or more floats 270 has a first known density $(\rho_1)$ and a second 270*b* of the two or more floats 270 has a second known density (ρ₂) greater than the first known density (ρ₁). Further to the embodiment of FIG. 2, a third 270*c* of the two or more floats 270 has a third known density (ρ₃) greater than the second known density (ρ₂), and a fourth 270*d* of the two or more floats 270 has a fourth known density (ρ₄) greater than the third known density (ρ₃).

Depending on the accuracy wanted and/or necessary, the two or more floats 270 may have various different densities, and the gap between the various different densities change. For example, in at least one embodiment wherein the density sensor 250 includes three floats, the three floats might have a density ranging from 0.6 sg to 1.2 sg. In yet another embodiment wherein the density sensor 250 includes four floats, the four floats might have a density ranging from 0.7 sg to 1.1 sg. Further to the four float design, the first known density (ρ₁) might range from 7 sg to 0.79 sg, the second known density (ρ₂) might range from 0.8 sg to 0.89 sg, the third known density (ρ₃) might range from 0.9 sg to 0.99 sg, and the fourth known density (ρ₄) might range from 1.0 sg to 1.1 sg. The foregoing densities are well suited for ascertaining the water cut of the wellbore.

It should be clear that the two or more floats 270 do not need to be spheres, as shown in FIG. 2. The two or more floats 270 could alternatively be cylinders, tubes, etc. More volume increases the buoyancy force, which aids in detection. Also, while the two or more floats 270 are illustrated as free floating, other embodiments may exist wherein the two or more floats 270 are hinged. The hinged placement of the two or more floats 270 means that their movement is constrained, which might make sensor placement easier.

The density sensor 250, in accordance with at least one embodiment, may further include one or more sensors 280 located proximate the one or more float chambers 260. In accordance with this embodiment, the one or more sensors 280 are configured to sense whether ones of the two or more floats 270 sink or float within the production fluid having the unknown density (ρ_f). In the illustrated embodiment of FIG. 2, the density sensor 250 includes one or more float sensors 280*a* and one or more sink sensors 280*b*. The one or more sink sensors 280*b*, in the illustrated embodiment, are one or more redundant sink sensors, and thus provide redundant information (albeit opposite information) as the one or more float sensors 280*a*. In at least one other embodiment, the one or more float sensors 280*a* are one or more redundant float sensors. In yet another embodiment, only the one or more float sensors 280*a* are used, or alternatively only the one or more sink sensors 280*b* are used. Also, while a single float sensor 280*a* and single sink sensor 280*b* are illustrated in FIG. 2, other embodiment exist wherein each of the two or more floats 270 has a dedicated float and/or sink sensor.

The one or more sensors 280, in at least one embodiment, are one or more proximity sensors. In at least one embodiment, the one or more proximity sensors are one or more non-contact proximity sensors. For example, in at least one embodiment, the non-contact proximity sensor is an electronic sensor that can detect if the float is nearby. In one embodiment, the proximity sensor uses an AC electronic signal to detect the float. The AC signal from the proximity sensor, in one or more embodiments, can be an electric field from a capacitive sensor or a magnetic field from an inductive sensor. In at least one embodiment, the float would have metallic components that would increase the sensitivity to the AC signal. Other non-contact proximity sensors include acoustic proximity sensors and optical proximity sensors (optical could be possible in oil because it is not necessary to look extremely far into the fluid). An RFID tag on the float could be used to detect its proximity to the sensor. With an RFID detector, a single sensor could be used to record the buoyancy position of all of the floats. Furthermore, the RFID detector may allow for combining multiple floats into a single float chamber, rather than having separate float chambers for each float.

The aforementioned proximity sensors are non-contact proximity sensors. Nevertheless, other embodiments exist wherein the one or more sensors 280 are one or more contact proximity sensors, such as a contacting switch. The force of the float against the switch could be used to provide interpolation of the density of the production fluid. The contact switch may be a force sensor such as would be made with a strain gauge or with a spring, among others.

The density sensor 250, in accordance with at least one embodiment, may further include electronics 290 coupled to the one or more sensors 280. In accordance with one embodiment, the electronics 290 are configured to calculate an approximation for the unknown density (ρ_f) of the production fluid based upon sensed values of whether ones of the two or more floats 270 sink or float within the production fluid. Data from the one or more sensors 280 and electronics 290 may be relayed to the surface using various different telemetry. In at least one embodiment, the telemetry is wired telemetry, such as an electric line, an optical line, or a hydraulic line. In yet one other embodiment, the telemetry is wireless telemetry. In certain embodiments, the electronics 290 that calculate the approximation for the unknown density (ρ_f) of the production fluid are located downhole. For example, the approximation information can be used locally in a feedback control of the inflow control device, such as the AICD. In yet another embodiment, the electronics 290 that calculate the approximation for the unknown density (ρ_f) are located uphole, and receive the information from the telemetry.

While not illustrated, the downhole tool 200 could further include a temperature sensor. The temperature of the fluid changes as the fluid passes through the inflow control device of the downhole tool 200. This Joule-Thomson temperature change is generally much larger for gas than it would be for liquids. Thus, we can help refine the gas cut in our system by noting the density as well as the Joule-Thomson temperature change. The temperature changes as the pressure changes. The pressure change can be at a restriction associated with our sensor or at a restriction elsewhere in the flow path (such as an ICD, ICV, AICD, etc.).

Figure 3A:
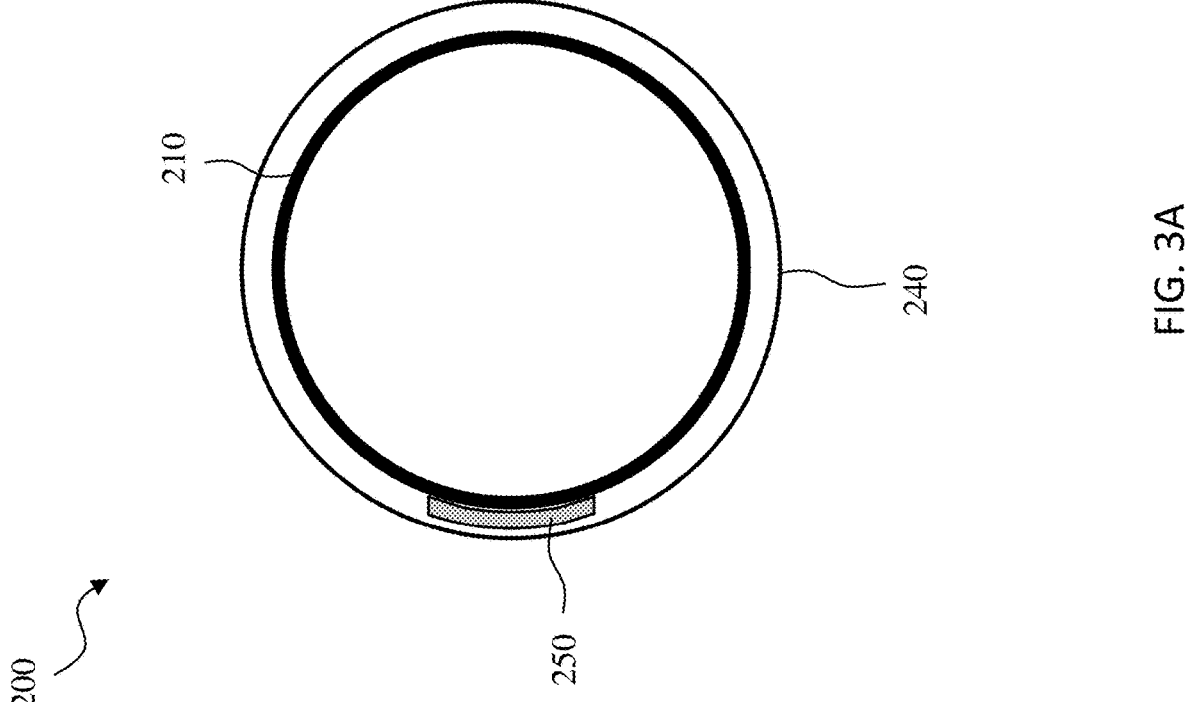
FIG. 3A illustrates a cross-sectional view of the downhole tool of FIG. 2 taken through the line 3A-3A.
Figure 3B:
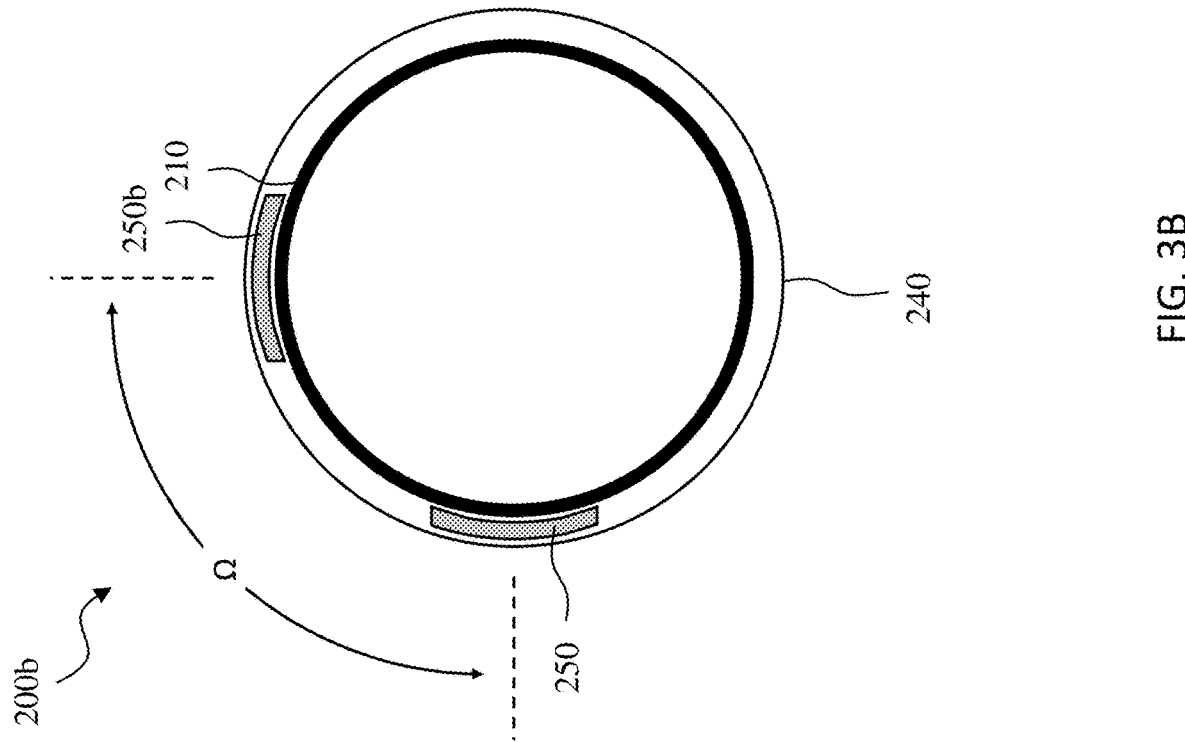
FIG. 3B illustrates an optional embodiment illustrating that a second density sensor may be added to the downhole tool.

Turning to FIG. 3A, illustrated is a cross-sectional view of the downhole tool 200 of FIG. 2 taken through the line 3A-3A. As shown in FIG. 3A, the downhole tool 200 includes a single density sensor 250, for example located at 9'olock. In another optional embodiment, such as that shown in FIG. 3B, a second density sensor 250*b* may be added to the downhole tool 200*b*. The inclusion of the second density sensor 250*b* allows for the downhole tool 200*b* to cover all of the possible downhole orientations in a horizontal well. In at least one embodiment, the first density sensor 250 and the second density sensor 250*b* are radially offset from one another by an angle (Ω) ranging from 60 degrees to 120 degrees. In yet another embodiment, the first density sensor 250 and the second density sensor 250*b* are radially offset from one another by an angle (Ω) ranging from 75 degrees to 105 degrees, if not by an angle (Ω) ranging from 85 degrees to 95 degrees.

Turning now to FIGS. 4A through 4E, illustrated are different operational states for a density sensor 400 that has production fluid having an unknown density (ρ_f) passing therethrough. The density sensor 400, in at least one embodiment, includes four separate float chambers 410*a*, 410*b*, 410*c*, 410*d*, as well as four separate floats 420*a*, 420*b*, 420*c*, 420*d* located within the four separate float chambers 410*a*, 410*b*, 410*c*, 410*d*. In the illustrated embodiment of FIGS. 4A through 4E, the first float 420*a* has a first density of 0.7 sg, the second float 420*b* has a second greater density of 0.8 sg, the third float 420*c* has a third greater density of 0.9 sg, and the fourth float 420*d* has a fourth greater density of 1.0 sg. The density sensor 400, in the embodiment of FIGS. 4A through 4E, additionally includes four separate top sensors 430*a*, 430*b*, 430*c*, 430*d*, as well as four separate bottom sensors 440*a*, 440*b*, 440*c*, 440*d*. While not shown, electronics may couple to the four separate top sensors 430*a*, 430*b*, 430*c*, 430*d*, as well as the four separate bottom sensors 440*a*, 440*b*, 440*c*, 440*d*, for example to calculate an approximation for the unknown density ($\rho_f$) of the production fluid based upon sensed values of whether ones of the four separate floats 420*a*, 420*b*, 420*c*, 420*d* sink or float within the production fluid.

Figure 4A:
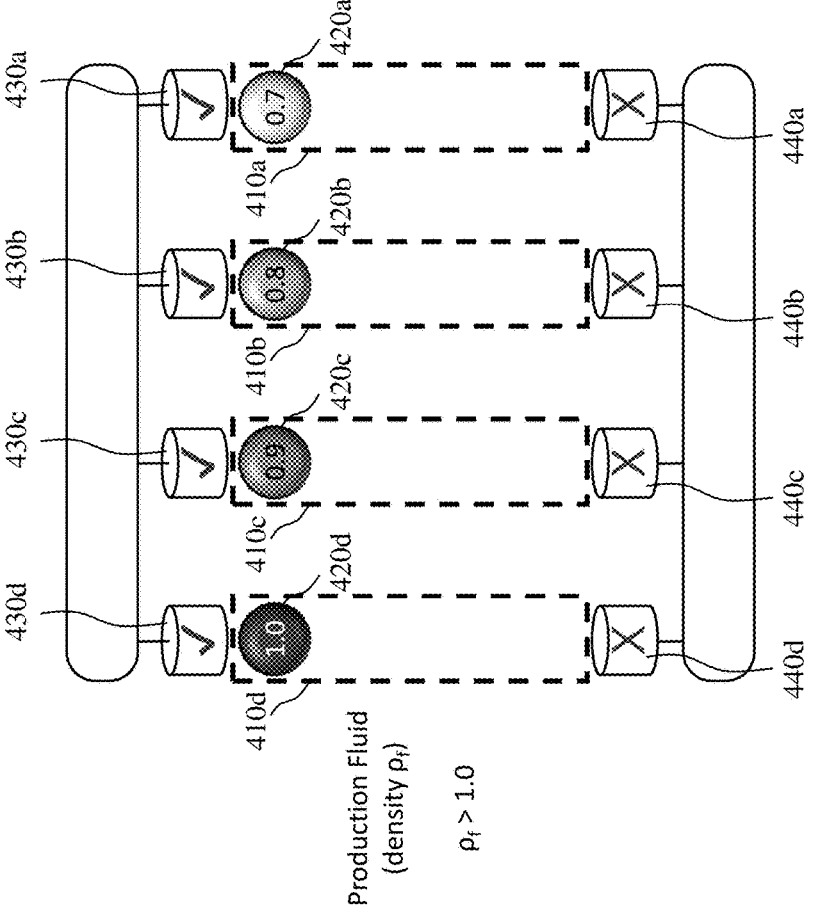
FIGS. 4A through 4E illustrate different operational states for a density sensor that has production fluid having an unknown density ($\rho$f) passing therethrough.

With initial reference to FIG. 4A, when subjected to production fluid having an unknown density ($\rho_f$), all of the four separate floats 420*a*, 420*b*, 420*c*, 420*d* float within their respective four separate float chambers 410*a*, 410*b*, 410*c*, 410*d*. Accordingly, the four separate floats 420*a*, 420*b*, 420*c*, 420*d* are in proximity (e.g., non-contact proximity or contact proximity) with the four separate top sensors 430*a*, 430*b*, 430*c*, 430*d*, and are not in proximity with the four separate bottom sensors 440*a*, 440*b*, 440*c*, 440*d*. Accordingly, the electronics coupled to the sensors can approximate (e.g., determine) that the unknown density ($\rho_f$) passing therethrough is greater than the most dense float (e.g., fourth float 420*d*), and thus the unknown density ($\rho_f$) is greater than 1.0 sg.

Figure 4B:
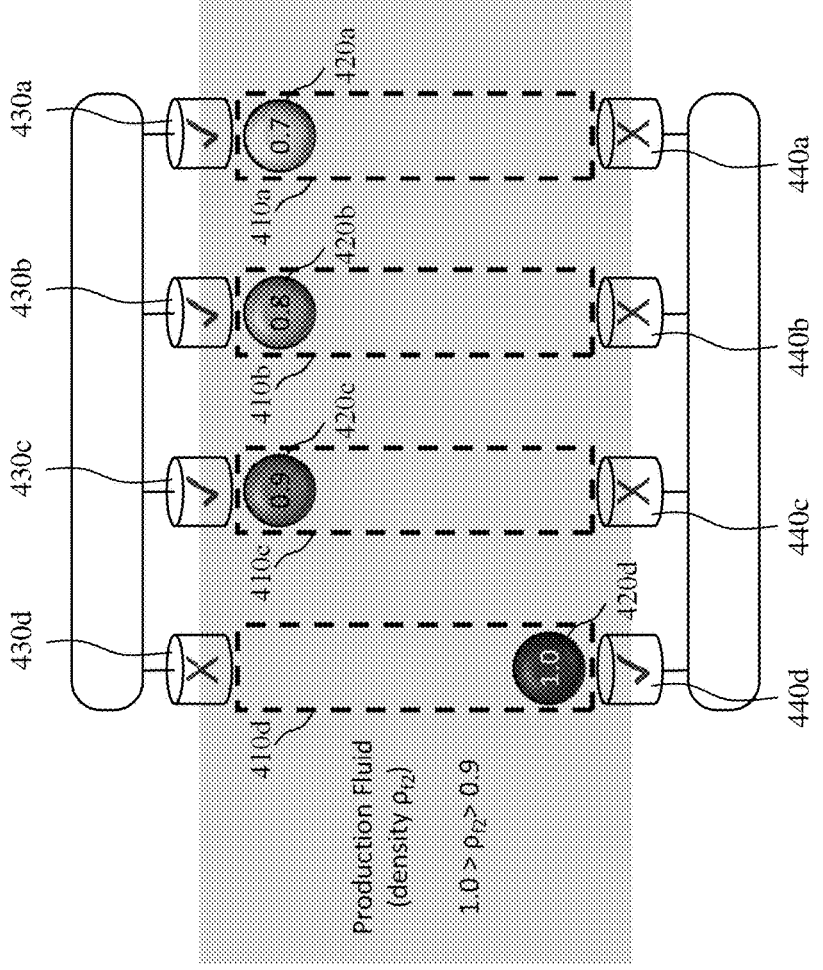

With continued reference to FIG. 4B, when subjected to production fluid having an unknown density ($\rho_{f2}$), the fourth float 420*d* sinks within its respective chamber 410*d*, while the other three floats 420*a*, 420*b*, 420*c*, float within their respective separate float chambers 410*a*, 410*b*, 410*c*. Accordingly, the electronics coupled to the sensors can approximate (e.g., determine) that the unknown density ($\rho_{f2}$) passing therethrough is greater than the second most dense float (e.g., third float 420*c*) but less than the most dense float (e.g., fourth float 420*d*), and thus the unknown density ($\rho_{f2}$) is between 1.0 sg and 0.9 sg.

Figure 4C:
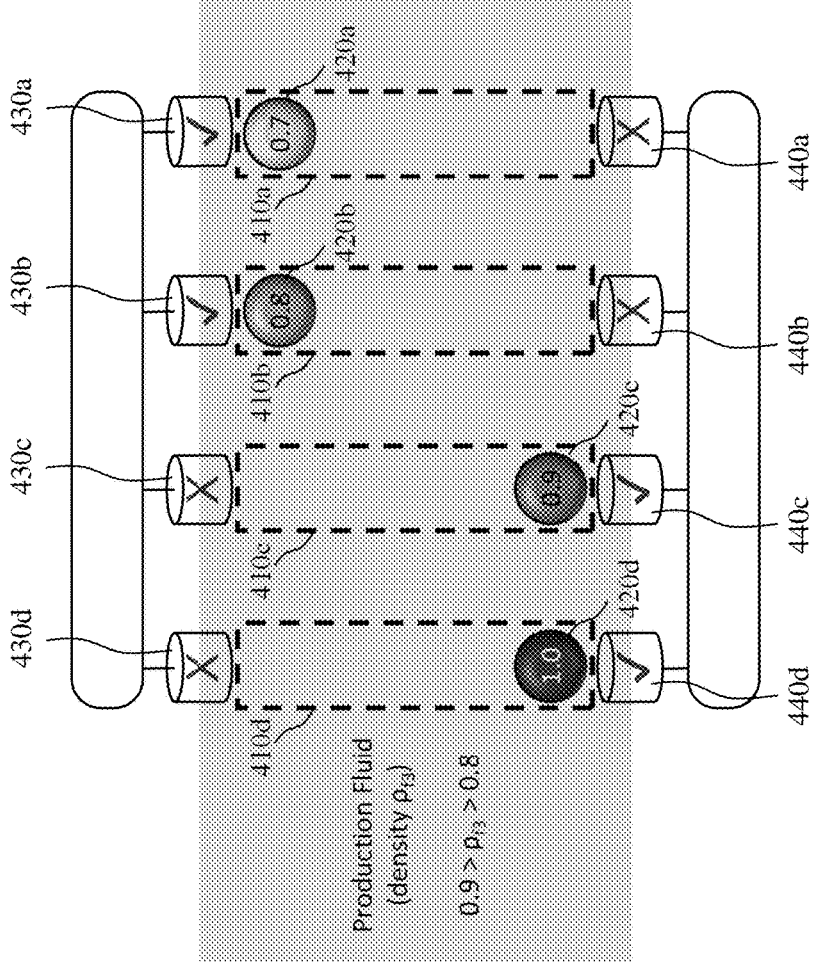

With continued reference to FIG. 4C, when subjected to production fluid having an unknown density ($\rho_{f3}$), the fourth float 420*d* and the third float 420*c* sink within their respective chambers 410*d*, 410*c* while the other two floats 420*a*, 420*b* float within their respective separate float chambers 410*a*, 410*b*. Accordingly, the electronics coupled to the sensors can approximate (e.g., determine) that the unknown density ($\rho_{f3}$) passing therethrough is greater than the third most dense float (e.g., second float 420*b*) but less than the second most dense float (e.g., third float 420*c*), and thus the unknown density ($\rho_{f3}$) is between 0.9 sg and 0.8 sg.

Figure 4D:
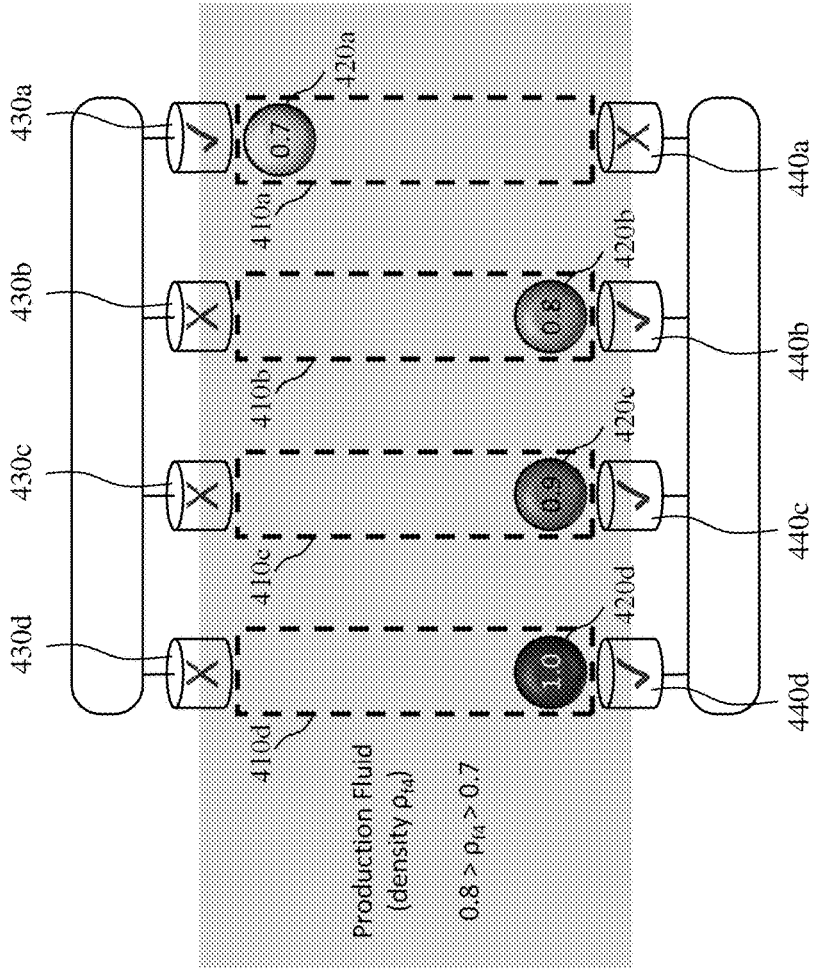

With continued reference to FIG. 4D, when subjected to production fluid having an unknown density ($\rho_{f4}$), the fourth float 420*d*, the third float 420*c* and the second float 420*b* sink within their respective chambers 410*d*, 410*c*, 410*b* while the first float 420*a* floats within its respective separate float chamber 410*a*. Accordingly, the electronics coupled to the sensors can approximate (e.g., determine) that the unknown density ($\rho_{f4}$) passing therethrough is greater than the fourth most dense float (e.g., first float 420*a*) but less than the third most dense float (e.g., second float 420*b*), and thus the unknown density ($\rho_{f4}$) is between 0.8 sg and 0.7 sg.

Figure 4E:
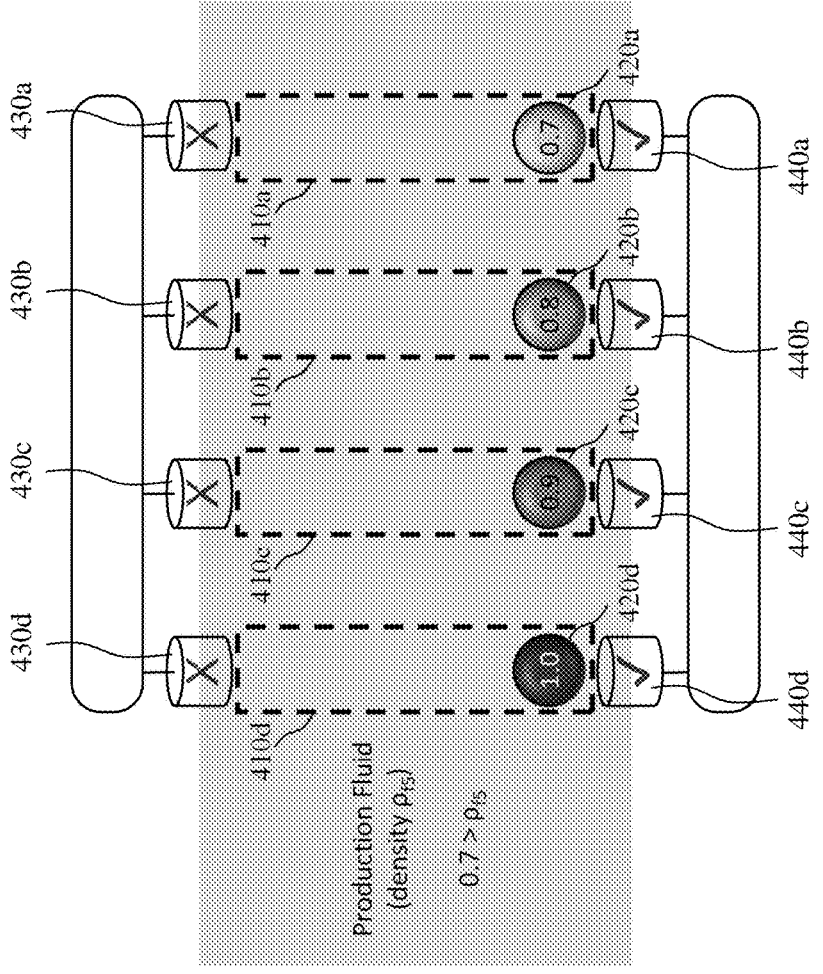
Figure 4E:

With continued reference to FIG. 4E, when subjected to production fluid having an unknown density ($\rho_{f5}$), all the floats 420*d*, 420*c*, 420*b*, 420*a* sink within their respective chambers 410*d*, 410*c*, 410*b*, 410*a*. Accordingly, the electronics coupled to the sensors can approximate (e.g., determine) that the unknown density ($\rho_{f5}$) passing therethrough is less than the fourth most dense float (e.g., first float 420*a*), and thus the unknown density ($\rho_{f5}$) is less than 0.7 sg.

The present disclosure has recognized that in some embodiments, the above-mentioned concepts are enhanced by the rotation of the density sensor. Typically, the buoyancy force generated by the float is small because the difference in density between the lower-density fluid and the higher-density fluid is generally small, and there is only a small amount (e.g., 5 milli-Newtons) of gravitational force acting on this difference in density. This makes the density sensor sensitive to orientation, which may cause the float to get stuck in the sink or the float position. However, rotation of density sensor creates a force (e.g., a centripetal force or a centrifugal force) on the floats. The force acts as artificial gravity that is much higher than the small gravitational force naturally acting on the difference in density. This allows the density sensor to more reliably move between the sink and float positions based on the density of the fluid. This also makes the density sensor perform in a manner that is insensitive to orientation, because the force generated by the rotatable component is much larger than the naturally occurring gravitational force.

Turning now to FIGS. 5A through 5F, illustrated are different operational states for an alternative embodiment of a density sensor 500 that has production fluid having an unknown density ($\rho_f$) passing therethrough. The density sensor 500 could be positioned in a similar location in a downhole tool as the density sensor 200 of FIG. 2. The density sensor 500, in at least one embodiment, includes a rotating centrifuge 505. The rotating centrifuge 505, in at least the illustrated embodiment, has five separate float chambers 510*a*, 510*b*, 510*c*, 510*d*, 510*e* located therein. The density sensor 500 additionally includes five separate floats 520*a*, 520*b*, 520*c*, 520*d*, 520*e* located within the five separate float chambers 510*a*, 510*b*, 510*c*, 510*d*, 510*e*. In at least one embodiment, the rotating centrifuge 505 is configured to rotate based upon the production fluid passing thereby, and in doing so is configured to increase the buoyance force of the five separate floats 520*a*, 520*b*, 520*c*, 520*d*, 520*e*. While the rotating centrifuge 505 is illustrated with five float chambers 510*a*, 510*b*, 510*c*, 510*d*, 510*e* and five separate floats 520*a*, 520*b*, 520*c*, 520*d*, 520*e*, other embodiments employing two or more float chambers and two or more floats are within the scope of the disclosure.

In the illustrated embodiment of FIGS. 5A through 5F, the first float 520*a* has a first density of 0.7 sg, the second float 520*b* has a second greater density of 0.8 sg, the third float 520*c* has a third greater density of 0.85 sg, the fourth float 520*d* has a fourth greater density of 0.9 sg, and the fifth float 520*e* has a fifth greater density of 1.0 sg. The density sensor 500, in the embodiment of FIGS. 5A through 5F, additionally includes five separate sensor (not shown) for sensing the sinking or floating of the floats 520*a*, 520*b*, 520*c*, 520*d*, 520*e*. The term "float" as used in this rotating embodiment, means that the five separate floats 520*a*, 520*b*, 520*c*, 520*d*, 520*e* are in their radially retracted state. In contrast, the term "sink" as used in this rotating embodiment, means that the five separate floats 520*a*, 520*b*, 520*c*, 520*d*, 520*e* are in their radially extended state. While also not shown, electronics will couple to the five separate sensors, for example to calculate an approximation for the unknown density ($\rho_f$) of the production fluid based upon sensed values of whether ones of the five separate floats 520a, 520b, 520c, 520d, 520e sink or float within the production fluid.

Figure 5A:
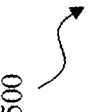
FIGS. 5A through 5F illustrate different operational states for an alternative embodiment of a density sensor that has production fluid having an unknown density ($\rho$f) passing therethrough.

With initial reference to FIG. 5A, when subjected to production fluid having an unknown density ($\rho_f$), all of the five separate floats 520a, 520b, 520c, 520d, 520e float within their respective five separate float chambers 510a, 510b, 510c, 510d, 510e. In this embodiment, the five separate sensors (not shown) and electronics (not shown) coupled thereto, can approximate (e.g., determine) that the unknown density ($\rho_f$) passing therethrough is greater than the most dense float (e.g., fifth float 520e), and thus the unknown density ($\rho_f$) is greater than 1.0 sg.

Figure 5B:
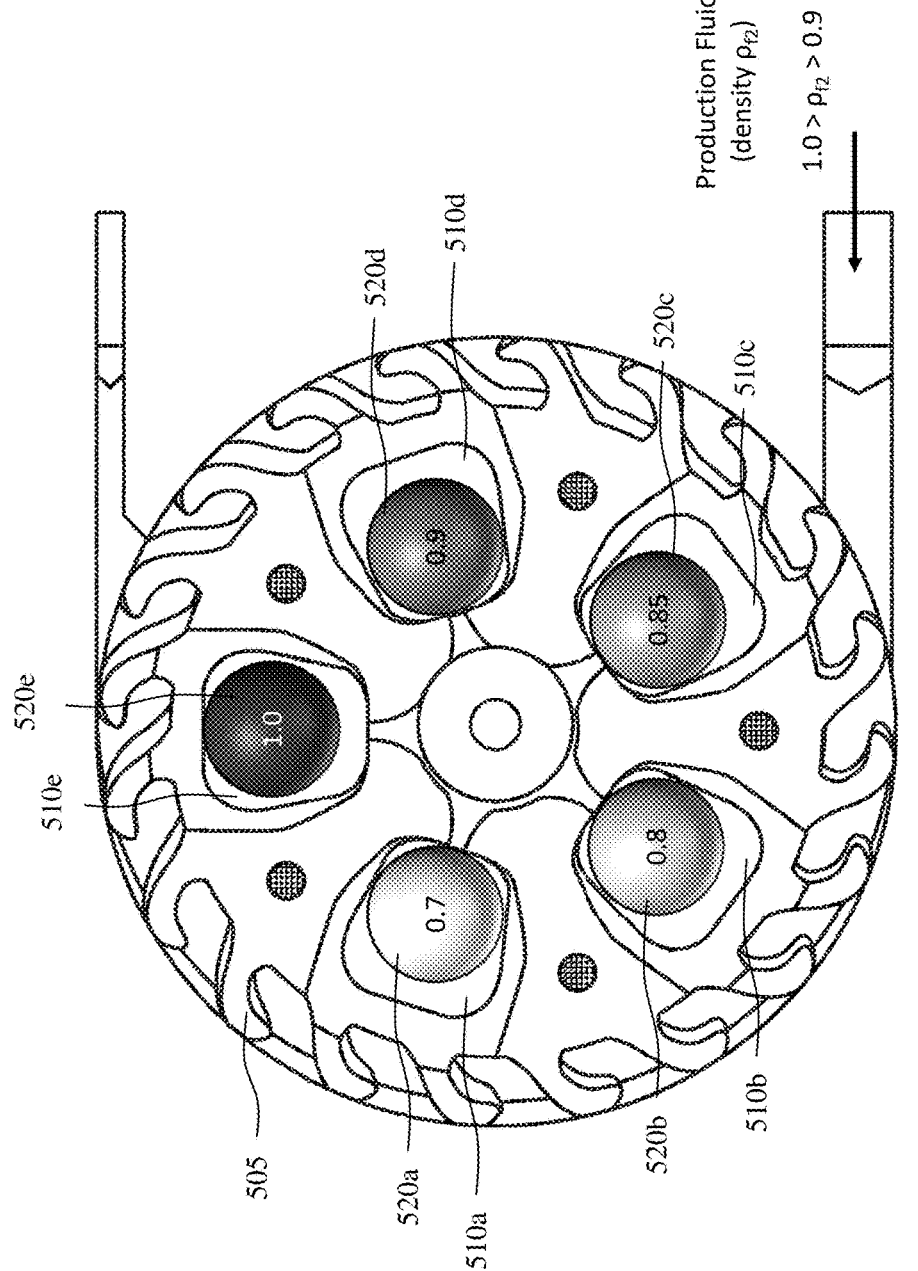
Figure 5B:
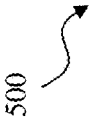

With continued reference to FIG. 5B, when subjected to production fluid having an unknown density ($\rho_{f2}$), the fifth float 520e sinks within its respective chamber 510e, while the other four floats 520a, 520b, 520c, 520d float within their respective separate float chambers 510a, 510b, 510c, 510d. Accordingly, the electronics coupled to the sensors can approximate (e.g., determine) that the unknown density ($\rho_{f2}$) passing therethrough is greater than the second most dense float (e.g., fourth float 520d) but less than the most dense float (e.g., fifth float 520e), and thus the unknown density ($\rho_{f2}$) is between 1.0 sg and 0.9 sg.

Figure 5C:
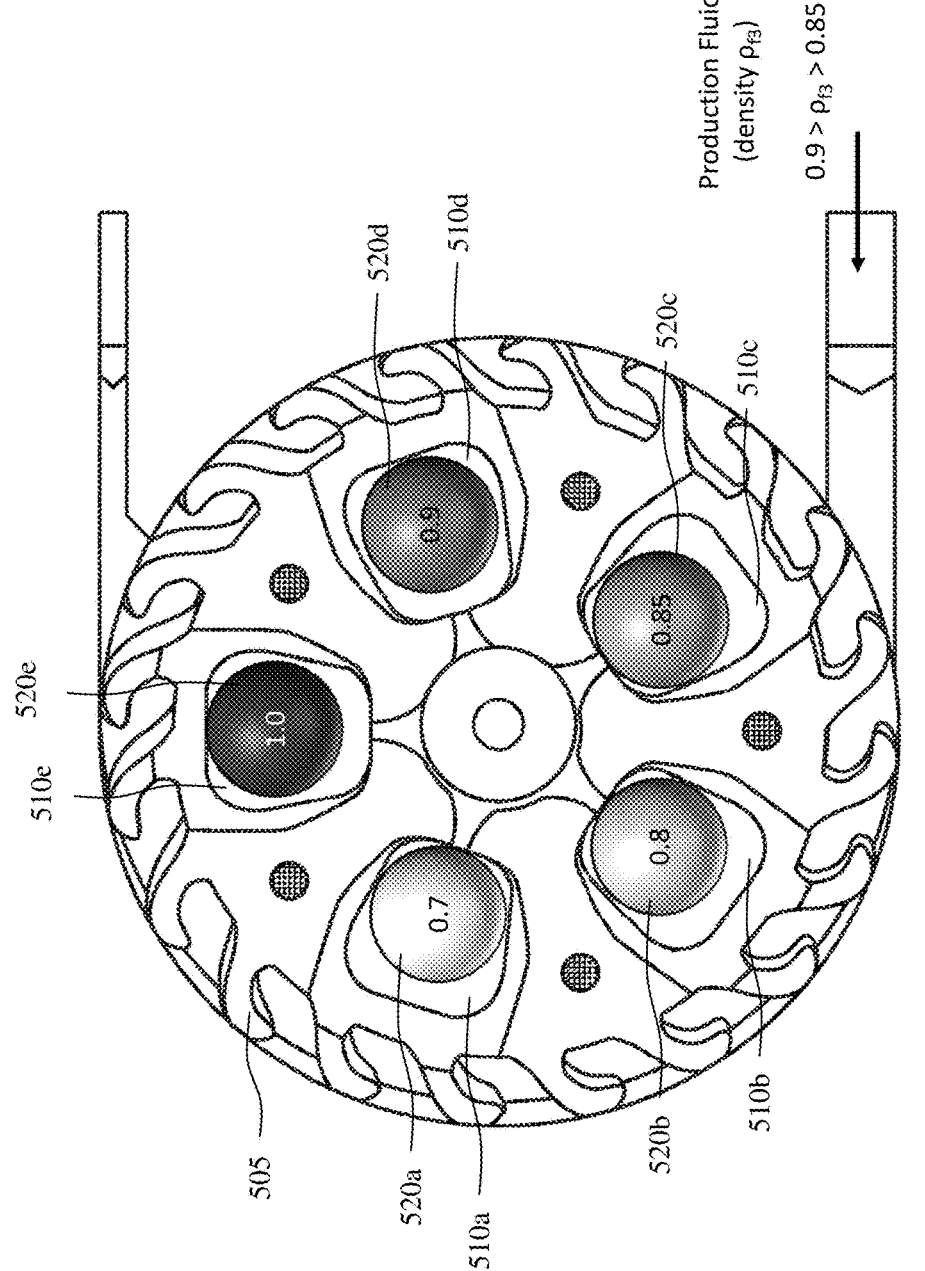
Figure 5C:

With continued reference to FIG. 5C, when subjected to production fluid having an unknown density ($\rho_{f3}$), the fifth float 520e and the fourth float 520d sink within their respective chambers 510e, 510d while the other three floats 520a, 520b, 520c, float within their respective separate float chambers 510a, 510b, 510c. Accordingly, the electronics coupled to the sensors can approximate (e.g., determine) that the unknown density ($\rho_{f3}$) passing therethrough is greater than the third most dense float (e.g., third float 520c) but less than the second most dense float (e.g., fourth float 520d), and thus the unknown density ($\rho_{f3}$) is between 0.9 sg and 0.85 sg.

Figure 5D:
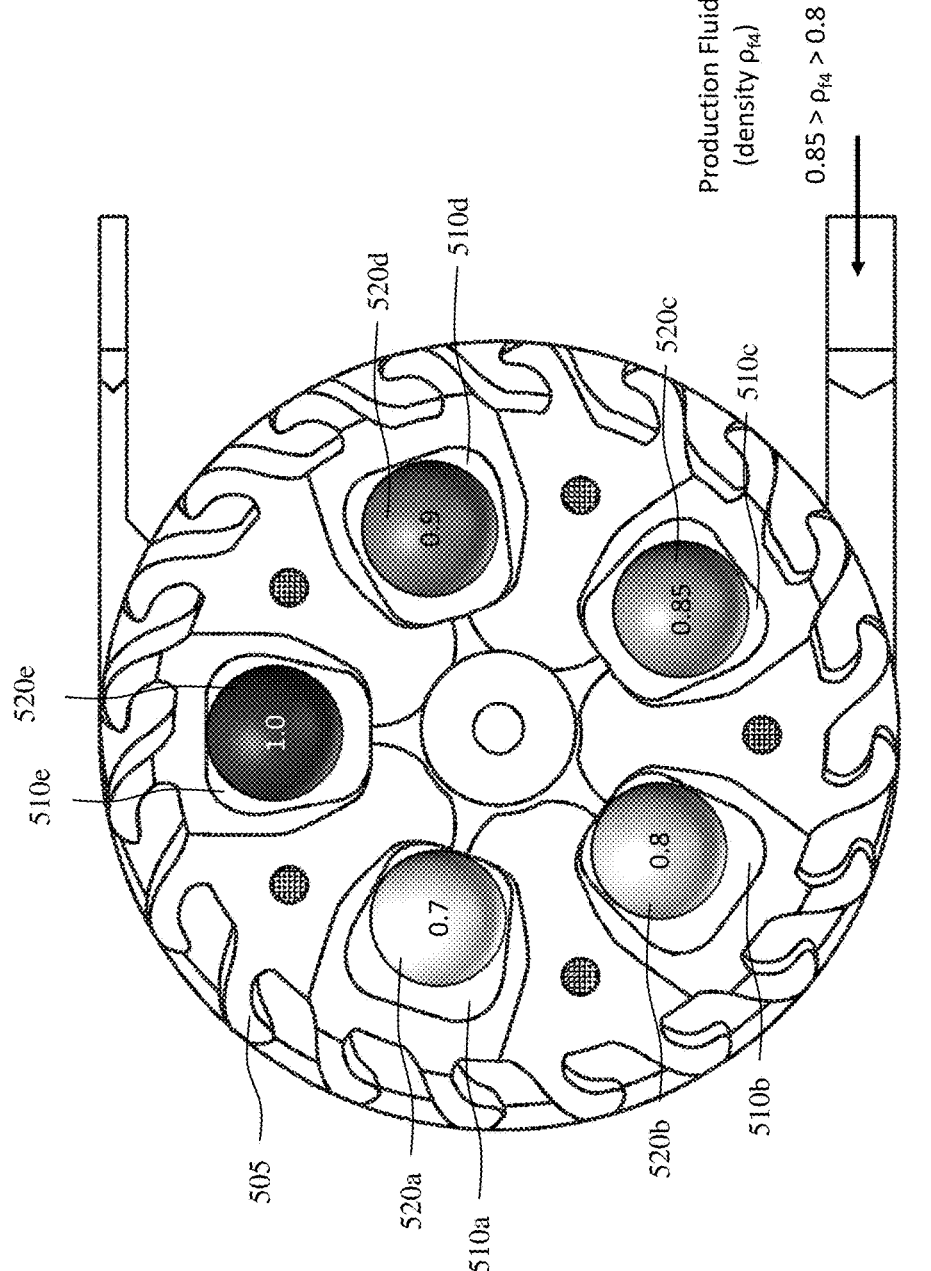

With continued reference to FIG. 5D, when subjected to production fluid having an unknown density ($\rho_{f4}$), the fifth float 520e, fourth float 520d and third float 520c sink within their respective chambers 510e, 510d, 510c while the other two floats 520a, 520b, float within their respective separate float chambers 510a, 510b. Accordingly, the electronics coupled to the sensors can approximate (e.g., determine) that the unknown density ($\rho_{f4}$) passing therethrough is greater than the fourth most dense float (e.g., second float 520b) but less than the third most dense float (e.g., third float 520c), and thus the unknown density ($\rho_{f4}$) is between 0.85 sg and 0.8 sg.

Figure 5E:
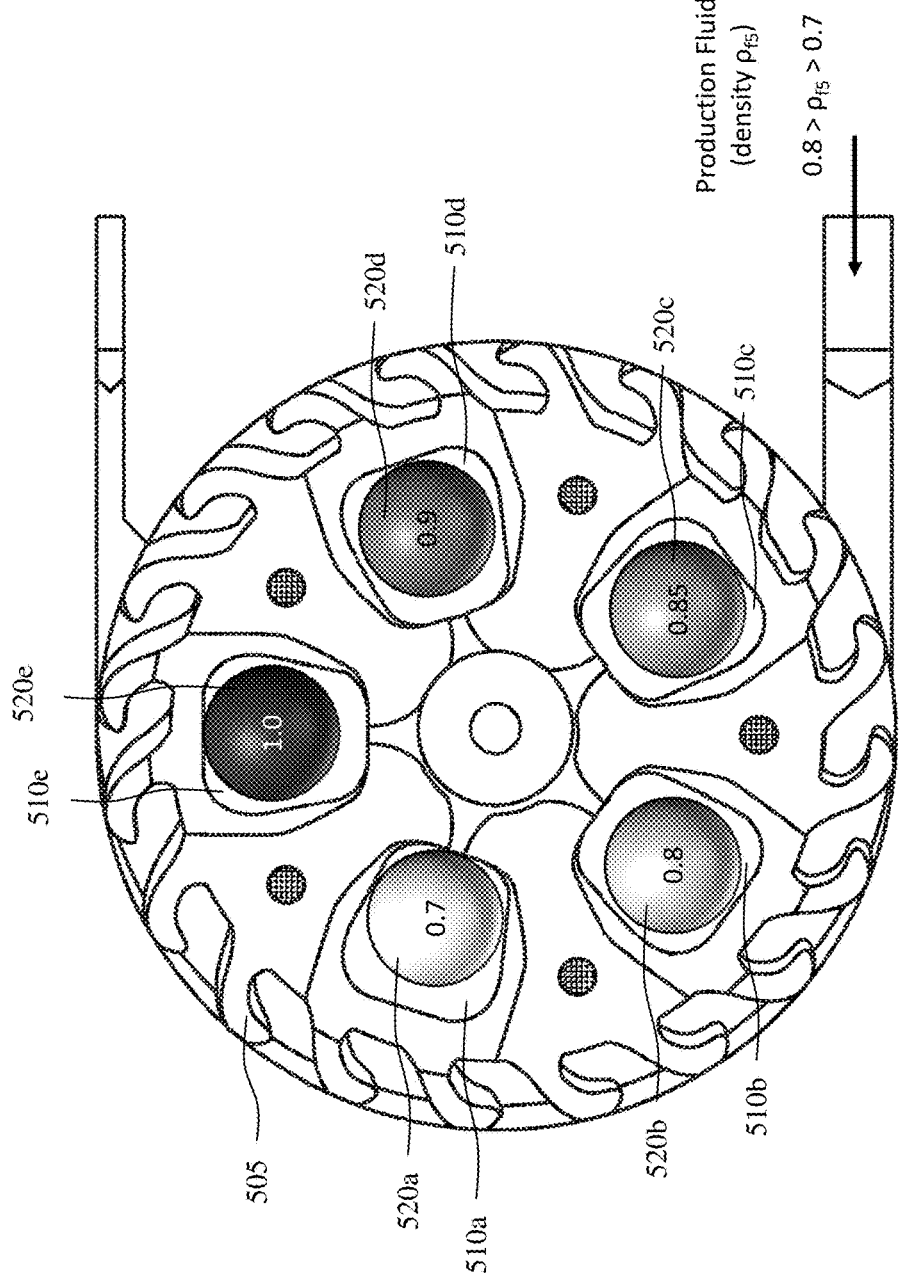
Figure 5E:
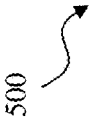

With continued reference to FIG. 5E, when subjected to production fluid having an unknown density ($\rho_{f5}$), the fifth float 520e, the fourth float 520d, the third float 520c and the second float 520b sink within their respective chambers 510e, 510d, 510c, 510b while the first float 520a floats within its respective separate float chamber 510a. Accordingly, the electronics coupled to the sensors can approximate (e.g., determine) that the unknown density ($\rho_{f5}$) passing therethrough is greater than the fifth most dense float (e.g., first float 520a) but less than the fourth most dense float (e.g., second float 520b), and thus the unknown density ($\rho_{f5}$) is between 0.8 sg and 0.7 sg.

Figure 5F:
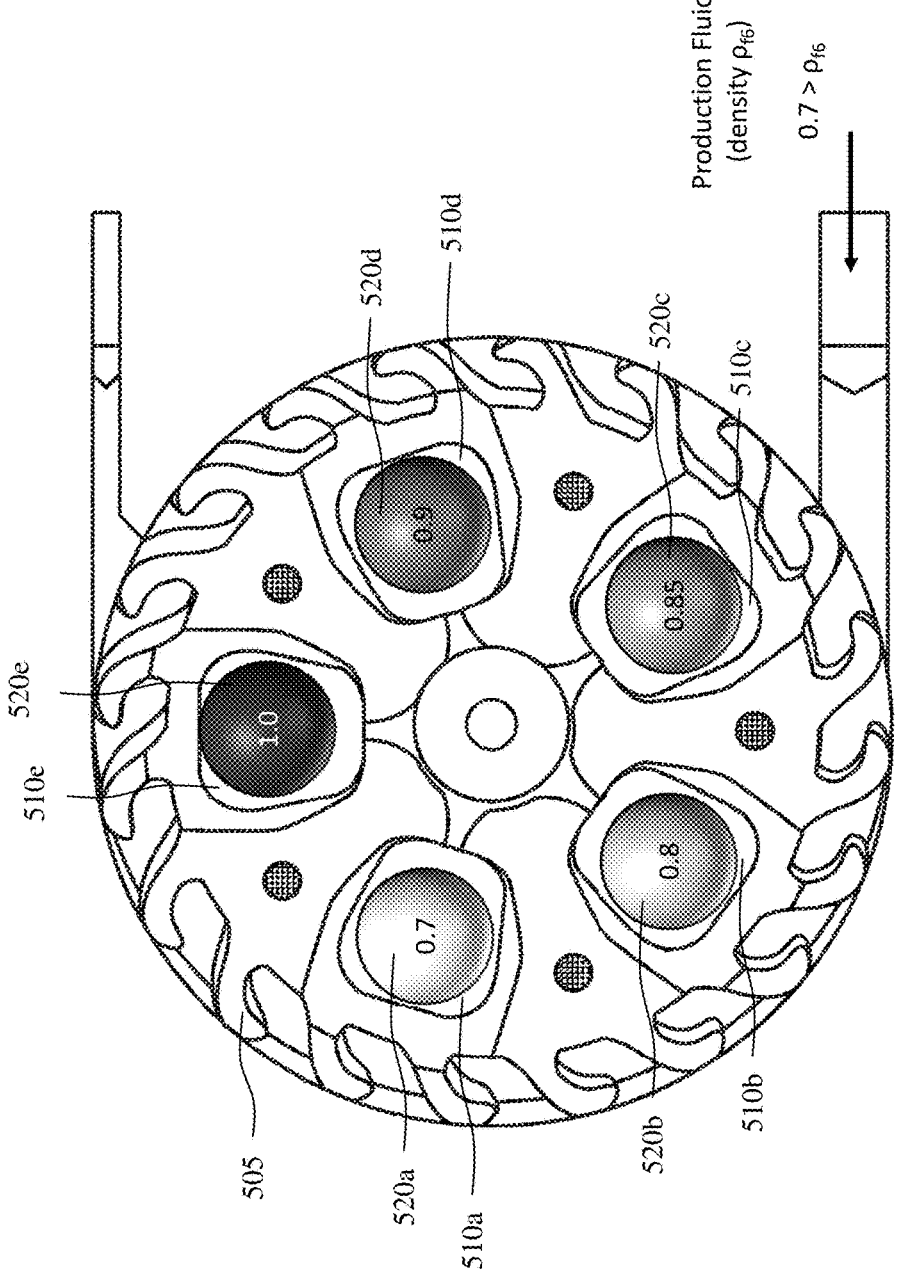
Figure 5F:
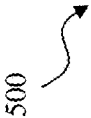

With continued reference to FIG. 5F, when subjected to production fluid having an unknown density ($\rho_{f6}$), all the floats 520e, 520d, 520c, 520b, 520a sink within their respective chambers 510e, 510d, 510c, 510b, 510a. Accordingly, the electronics coupled to the sensors can approximate (e.g., determine) that the unknown density ($\rho_{f6}$) passing therethrough is less than the fifth most dense float (e.g., first float 520a), and thus the unknown density ($\rho_{f6}$) is less than 0.7 sg.

Figure 6A:
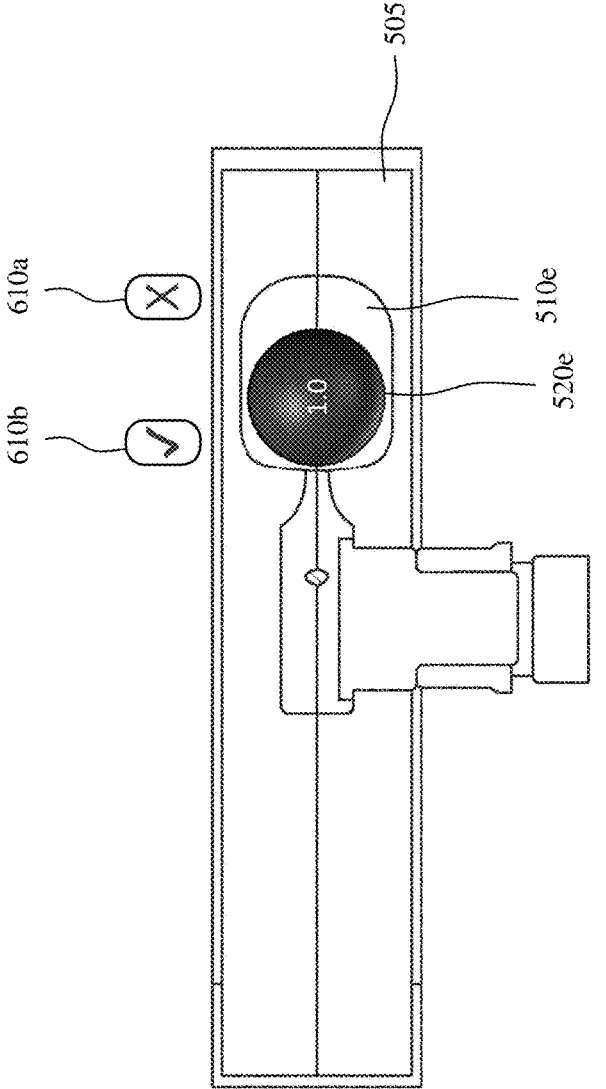
FIG. 6A illustrates a cross-sectional view of the density sensor of FIG. 5A taken through the line 6A-6A.

Turning to FIG. 6A, illustrated is a cross-sectional view of the density sensor 500 of FIG. 5A taken through the line 6A-6A. As shown in FIG. 6A, the density sensor 500 includes one or more sink sensors 610a and/or one or more float sensors 610b positioned along a face of the rotating centrifuge 505. In the illustrated embodiment, the one or more sink sensors 610a and/or one or more float sensors 610b are one or more non-contact proximity sensors. The non-contact proximity sensors allow the rotating centrifuge 505 to rotate while continuing to sense the sinking and/or floating of the floats 520a-520e. In this embodiment, the one or more sink sensors 610a and/or one or more float sensors 610b would look for "blips" as the centrifuge rotated next to the sensors. The one or more sink sensors 610a would count their number of pulses and the one or more float sensors 610b would count their pulses. The ratio of pulses could indicate the placement of the floats.

Figure 6B:
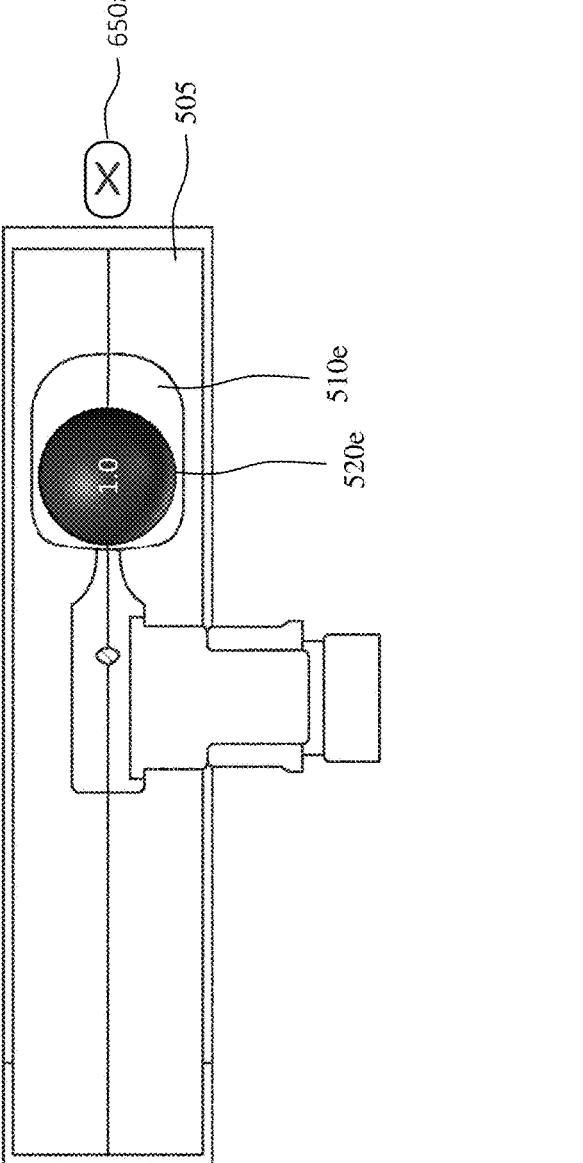
FIG. 6B illustrates a cross-sectional view of an alternative embodiment of the density sensor of FIG. 5A taken through the line 6A-6A.

In another optional embodiment, such as that shown in FIG. 6B, one or more sink sensors 650a are located along an end of the rotating centrifuge 505.

Figure 7A:
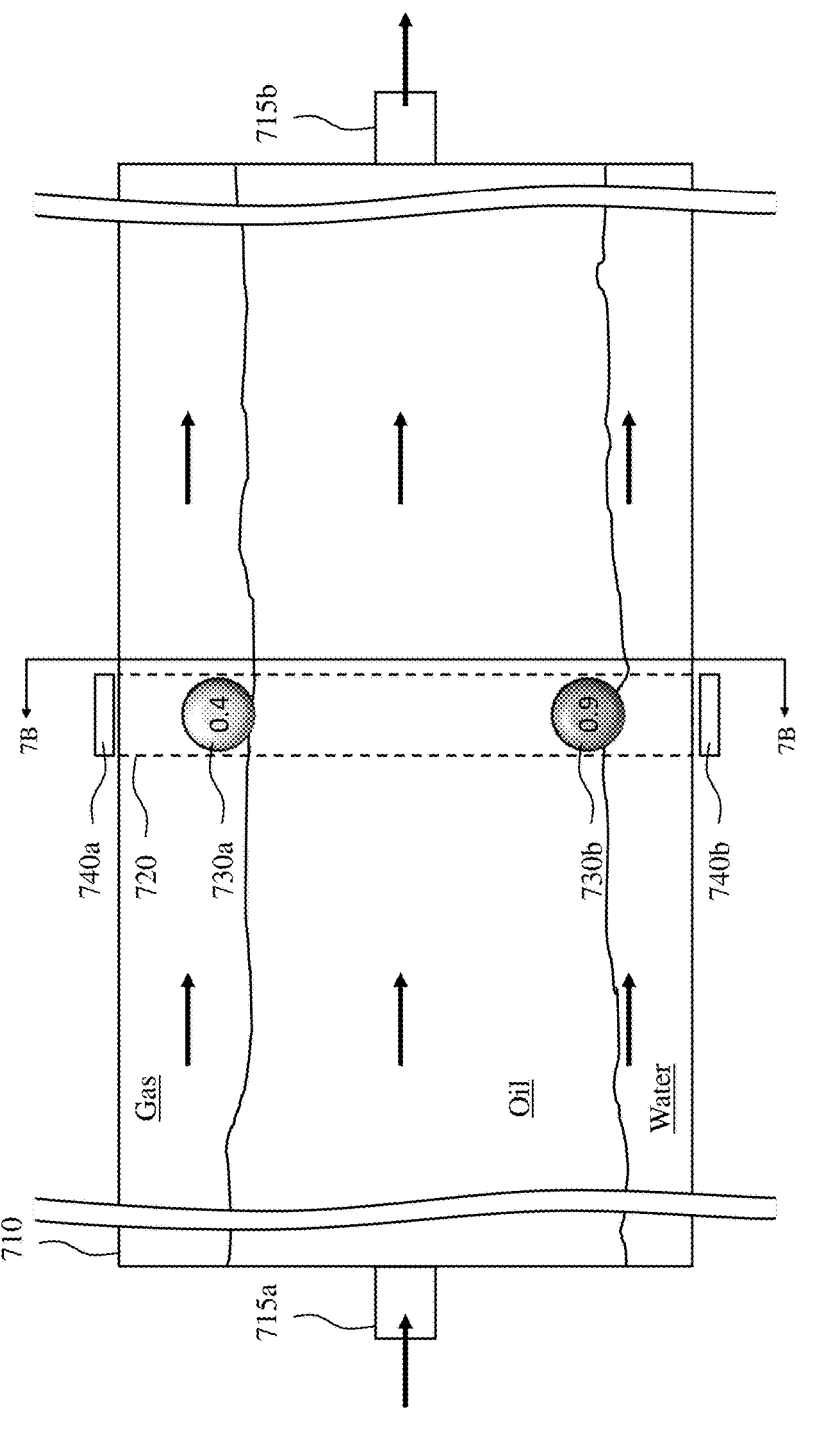
FIGS. 7A and 7B illustrate various different views of a downhole tool designed, manufactured and/or operated according to one or more alternative embodiments of the disclosure.
Figure 7B:
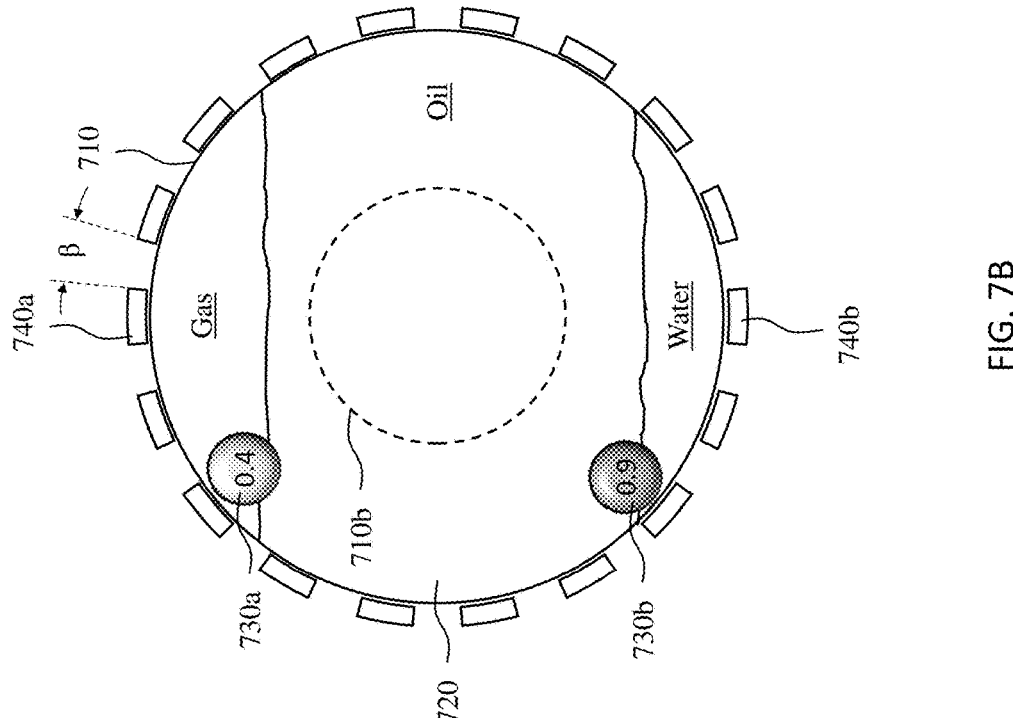

Turning to FIGS. 7A and 7B, illustrated are various different views of a downhole tool 700 designed, manufactured and/or operated according to one or more alternative embodiments of the disclosure. The downhole tool 700, in at least one embodiment, may be employed to approximate a composition (e.g., percentage composition of the various different components) of production fluid having an unknown composition travelling within a wellbore. The downhole tool 700, in one embodiment, includes a tubular 710 providing one or more production fluid flow paths (e.g., as shown by the arrows) for a production fluid having an unknown composition. In at least one embodiment, the tubular 710 is designed (e.g., in size, volume, etc.) to provide a flow rate low enough that the production fluid may separate into its various different components (e.g., gas, oil, water, mud, etc.). In at least one embodiment, the tubular 710 is a long and high volume tubular, such that the production fluid may separate into its separate components. Those skilled in the art understand the various different features, techniques and methods that could be used to cause the production fluid to separate into its components.

In the illustrated embodiment, the downhole tool 700 includes a single fluid inlet 715a, and a single fluid outlet 715b. In other embodiments, as will be discussed below, the downhole tool 700 may include multiple fluid inlets 715a and/or multiple fluid outlets 715b. In at least one embodiment, the multiple fluid inlets 715a assist the continuous turnover, and subsequent separation of the components of the production fluid over time and/or distance.

The downhole tool 700, in the embodiment of FIGS. 7A and 7B, additionally includes one or more float chambers 720 located within the tubular 710. The one or more float chambers 720, as will be appreciated below, may have a variety of different configurations and/or locations and remain within the scope of the disclosure. In the illustrated embodiment of FIGS. 7A and 7B, the downhole tool 700 employs only a single float chamber 720.

The tubular 710, in at least one embodiment, is a first tubular. In at least one other embodiment, the downhole tool 700 further includes a second tubular 710b positioned within the first tubular 710. As shown in FIGS. 7A and 7B, the one or more float chambers 720 are located within an annulus formed between the first tubular 710 and the second tubular 710b. Depending on the design of the downhole tool 700, the first tubular 710 may be wellbore casing and the second tubular 710b may be production tubing. In yet another embodiment, the first tubular 710 is an inner surface of a wellbore, and the second tubular 710b is production tubing. In yet another embodiment, the first tubular 710 is a radial outer housing, and the second tubular 710b is production tubing (e.g., as discussed above with regard to FIG. 2). While not shown in FIGS. 7A and 7B, but shown above with regard to FIG. 2, the downhole tool 700 may further include a wellbore screen positioned radially about the production tubing, the wellbore screen configured to receive the production fluid having the unknown composition and provide it to the annulus defined between the production tubing and the radial outer housing.

The downhole tool 700, in one or more embodiments, may additionally include two or more floats 730 located within the one or more float chambers 720. In accordance with one embodiment, a first 730a of the two or more floats has a first density ($\rho_1$) between a density of gas ($\rho_g$) and a density of oil ($\rho_o$). Accordingly, the first 730a of the two or more floats would settle at an interface wherein the oil meets the gas. Similarly, a second 730b of the two or more floats has a second density ($\rho_2$) between the density of oil ($\rho_o$) and a density of water ($\rho_w$). Accordingly, the second 730b of the two or more floats would settle at an interface wherein the oil meets the water. In the embodiment of FIGS. 7A and 7B, the first density ($\rho_1$) is 0.4 sg and the second density ($\rho_2$) is 0.9 sg. Nevertheless, in at least one other embodiment, the first density ($\rho_1$) may range from 0.2 sg to 0.7 sg, and the second density ($\rho_2$) may range from 0.85 sg to is 0.98 sg.

The downhole tool 700, in one or more other embodiments, may additionally include two or more non-contact proximity sensors 740a, 740b radially positioned about an outer surface of the tubular 910. In accordance with this embodiment, the two or more non-contact proximity sensors 740a, 740b are configured to sense a radial location of the two or more floats 730, such that a gas:oil ratio and oil:water ratio of the production fluid having the unknown composition may be approximated. For example, knowing the radial location of the two or more floats 730, as well as the area and/or shape of the tubular 910, a percentage of each of the constituents of the production fluid may also be approximated. Those skilled in the art understand the math necessary to make such approximations using the radial location of the two or more floats 730, however an example will be given below.

In the illustrated embodiment, the downhole tool 700 includes eight or more non-contact proximity sensors 740 equally radially positioned about an outer surface of the tubular 710. In yet another embodiment, the eight or more non-contact proximity sensors 740 are radially offset from one another by an angle (β) of less than 20 degrees. In even yet another embodiment, the eight or more non-contact proximity sensors are radially offset from one another by an angle (β) of less than 10 degrees, if not less than 5 degrees. In even another embodiment, the downhole tool 700 includes twelve or more non-contact proximity sensors 740 equally radially positioned about an outer surface of the tubular 710, if not eighteen or more non-contact proximity sensors 740 equally radially positioned about an outer surface of the tubular 710. The non-contact proximity sensors 740 may comprise any of the non-contact proximity sensors discussed above and remain within the scope of the present disclosure.

In at least one embodiment, the downhole tool includes electronics (not shown) coupled to the two or more non-contact proximity sensors 740a, 740b, the electronics configured to calculate the approximation for the gas:oil ratio and the oil:water ratio of the production fluid having the unknown composition.

Turning now to FIGS. 8A through 8C, illustrated are various different views of a downhole tool 800 designed, manufactured and/or operated according to one or more alternative embodiments of the disclosure. The downhole tool 800 is similar in many respects to the downhole tool 700. Accordingly, like reference numbers have been used to indicate similar, if not identical, features. The downhole tool 800 differs, for the most part, from the downhole tool 700, in that the two or more floats 730a, 730b are located in separate float chambers 820a, 820b. For example, the separate float chambers 820a, 820b may be configured as separate caged float chambers. Furthermore, the downhole tool 800 includes a second set of two or more non-contact proximity sensors 840a, 840b radially positioned about an outer surface of the tubular 710, the second set of two or more non-contact proximity sensors 840a, 840b configured to sense a radial location of the second float 730b.

FIGS. 8A through 8C provide a perfect example for calculating an approximation of the percentage of oil, gas and water travelling through the tubular 710. In the given example, let us assume a Diameter=12 cm, a Radius=6 cm, that $\theta_1$=80 degrees, and that $\theta_2$=120 degrees. Accordingly:

$$A_{Total} = \pi r^2 = 113 \text{ cm}^2$$

$$A_{Gas} = \text{Area of sector } OPQ - \text{Area of triangle } OPQ =$$

$$r^2\left(\frac{\pi\theta}{360} - \frac{\sin\theta}{2}\right) - \frac{1}{2}r^2\theta = 7.4 \text{ cm}^2$$

$$A_{Water} = \text{Area of sector } OST - \text{Area of triangle } OST =$$

$$r^2\left(\frac{\pi\theta}{360} - \frac{\sin\theta}{2}\right) - \frac{1}{2}r^2\theta = 22.1 \text{ cm}^2$$

$$A_{Oil} = A_{Total} - A_{Gas} - A_{Water} = 83.5 \text{ cm}^2$$

$$\text{Percentage Oil} = A_{Oil}/A_{Total} = 73.9\% \text{ Oil}$$

$$\text{Percentage Water} = A_{water}/A_{Total} = 19.6\% \text{ Water}$$

$$\text{Percentage Gas} = A_{Gas}/A_{Total} = 6.5\% \text{ Gas}$$

It should be recognized that if the two or more floats both float to the top and register with the highest most sensor (e.g., 740a in FIGS. 8A through 8C), the production fluid is primarily if not entirely water. Similarly, if the two or more floats both sink to the bottom and register with the lowest most sensor (e.g., 740b in FIGS. 8A through 8C), the production fluid is primarily if not entirely gas. Furthermore, if the first float 730a floats to the top and registers with the highest most sensor (e.g., 740a in FIGS. 8A through 8C) and the second float 730b sinks to the bottom and registers with the lowest most sensor (e.g., 740b in FIGS. 8A through 8C), the production fluid is primarily if not entirely oil. It should be further recognized that the foregoing is only an approximation of the relative percentages, as the values are dependent on the number of sensors, as well as the relative angular spacing therebetween. The greater the number of sensors, and thus the lesser angular spacing therebetween, the greater the accuracy of the approximation, which is a trade off the designer of the wellbore tool must make based upon many different criteria (e.g., cost, size, power consumption, etc.).

Turning now to FIGS. 9A and 9B, illustrated are various different views of a downhole tool 900 designed, manufactured and/or operated according to one or more alternative embodiments of the disclosure. The downhole tool 900 is similar in many respects to the downhole tool 700. Accordingly, like reference numbers have been used to indicate similar, if not identical, features. The downhole tool 900 differs, for the most part, from the downhole tool 700, in that the two or more floats 730a, 730b are fixed to an internal wire 910 located within the tubular 710. In this embodiment, each of the two or more floats 730a, 730b are configured to slide radially along the internal wire 910 as the unknown composition of the production fluid changes. In at least one embodiment, a change in resistance of the wire as the two or more floats 730a, 730b move may be measured to determine the radial location of the two or more floats 730a, 730b. For example, a process similar to a linear variable differential transformer, or a potentiometer that is changing the resistance of the wire as the two or more floats 730a, 730b move up and down may be used. Accordingly, it would not be necessary for the downhole tool 900 to include an extreme number of non-contact proximity sensors 740a, 740b, as one non-contact proximity sensors could measure multiple positions. The downhole tool 900 of FIGS. 9A and 9B additionally includes multiple fluid inlets 915a and fluid outlets 915b positioned at the ends of the tubing 710. Nevertheless, the multiple fluid inlets 915a and fluid outlets 915b could alternatively be positioned along the circumference of the tubing 710 as well.

Turning now to FIGS. 10A and 10B, illustrated are various different views of a downhole tool 1000 designed, manufactured and/or operated according to one or more alternative embodiments of the disclosure. The downhole tool 1000 is similar in many respects to the downhole tool 700. Accordingly, like reference numbers have been used to indicate similar, if not identical, features. The downhole tool 1000 differs, for the most part, from the downhole tool 700, in that the downhole tool 1000 includes a third float 1030c located within the one or more float chambers 720, the third float 1030c having a third density ($\rho_3$) between the density of water ($\rho_w$) and a density of mud ($\rho_m$). Accordingly, a water:mud ratio of the production fluid having the unknown composition may be approximated.

The downhole tool 1000, in the embodiment of FIGS. 10A and 10B, may additionally include an orientation float 1030d located within the one or more float chambers 720. Depending on the design of the downhole tool 1000, the orientation float 1030d has an orientation density ($\rho_{or}$) greater than a density of mud ($\rho_m$). Accordingly, the orientation float 1030d may be used as a reference point (e.g., calibration point) to approximate the gas:oil ratio and/or oil:water ratio and/or water:mud ratio of the production fluid having the unknown composition. In at least one embodiment, such as is shown in FIGS. 10A and 10B, the first density ($\rho_1$) ranges from 0.2 sg to 0.7 sg, the second density ($\rho_2$) ranges from 0.85 sg to 0.98 sg, the third density ($\rho_3$) ranges from 1.2 sg to 1.8 sg, and the orientation density ($\rho_{or}$) is at least 3.0 sg.

Aspects Disclosed Herein Include:

A. A density sensor, the density sensor including: 1) one or more float chambers; 2) two or more floats located within the one or more float chambers, the two or more floats having a density ranging from 0.08 sg to 2.1 sg, and further wherein a first of the two or more floats has a first known density ($\rho_1$) and a second of the two or more floats has a second known density ($\rho_2$) greater than the first known density ($\rho_1$); and 3) one or more sensors located proximate the one or more float chambers, the one or more sensors configured to sense whether ones of the two or more floats sink or float within production fluid having an unknown density ($\rho_f$).

B. A downhole tool, the downhole tool including: 1) a tubular providing one or more production fluid flow paths;

2) a density sensor positioned within the one or more production fluid flow paths, the density sensor including: a) one or more float chambers; b) two or more floats located within the one or more float chambers, the two or more floats having a density ranging from 0.08 sg to 2.1 sg, and further wherein a first of the two or more floats has a first known density ($\rho_1$) and a second of the two or more floats has a second known density ($\rho_2$) greater than the first known density ($\rho_1$); c) one or more sensors located proximate the one or more float chambers, the one or more sensors configured to sense whether ones of the two or more floats sink or float within production fluid having an unknown density ($\rho_f$); and d) electronics coupled to the one or more sensors, the electronics configured to calculate an approximation for the unknown density ($\rho_f$) based upon sensed values of whether ones of the two or more floats sink or float within the production fluid.

C. A well system, the well system including: 1) a wellbore formed through one or more subterranean formations; 2) a tubular positioned within the wellbore, the tubular providing one or more production fluid flow paths; 3) one or more inflow control devices coupled to the tubular, the one or more inflow control devices configured to provide production fluid from the one or more subterranean formations into the tubular; 4) one or more density sensors positioned within the one or more production fluid flow paths proximate the one or more inflow control devices, the one or more density sensors each including: a) one or more float chambers; b) two or more floats located within the one or more float chambers, the two or more floats having a density ranging from 0.08 sg to 2.1 sg, and further wherein a first of the two or more floats has a first known density ($\rho_1$) and a second of the two or more floats has a second known density ($\rho_2$) greater than the first known density ($\rho_1$); c) one or more sensors located proximate the one or more float chambers, the one or more sensors configured to sense whether ones of the two or more floats sink or float within production fluid having an unknown density ($\rho_f$); and d) electronics coupled to the one or more sensors, the electronics configured to calculate an approximation for the unknown density ($\rho_f$) based upon sensed values of whether ones of the two or more floats sink or float within the production fluid.

D. A downhole tool, the downhole tool including: 1) a tubular providing one or more production fluid flow paths for a production fluid having an unknown composition, the tubular designed to provide a flow rate low enough that the production fluid may separate into its components; 2) one or more float chambers located within the tubular; 3) two or more floats located within the one or more float chambers, a first of the two or more floats having a first density ($\rho_1$) between a density of gas ($\rho_g$) and a density of oil ($\rho_o$), and a second of the two or more floats having a second density ($\rho_2$) between the density of oil ($\rho_o$) and a density of water ($\rho w$); and 4) two or more non-contact proximity sensors radially positioned about an outer surface of the tubular, the two or more non-contact proximity sensors configured to sense a radial location of the two or more floats, such that a gas:oil ratio and oil:water ratio of the production fluid having the unknown composition may be approximated.

E. A well system, the well system including: 1) a wellbore formed through one or more subterranean formations; 2) a tubular positioned within the wellbore, the tubular providing one or more production fluid flow paths for a production fluid having an unknown composition, the tubular designed to provide a flow rate low enough that the production fluid may separate into its components; 3) one or more float chambers located within the tubular; 4) two or more floats located within the one or more float chambers, a first of the two or more floats having a first density ($\rho_1$) between a density of gas ($\rho_g$) and a density of oil ($\rho_o$), and a second of the two or more floats having a second density ($\rho_2$) between the density of oil ($\rho_o$) and a density of water ($\rho_w$); 5) two or more non-contact proximity sensors radially positioned about an outer surface of the tubular, the two or more non-contact proximity sensors configured to sense a radial location of the two or more floats, such that a gas:oil ratio and oil:water ratio of the production fluid having the unknown composition may be approximated; and 6) electronics coupled to the two or more sensors, the electronics configured to calculate the approximation for the gas:oil ratio and the oil:water ratio of the production fluid having the unknown composition.

Aspects A, B, C, D and E may have one or more of the following additional elements in combination: Element 1: further including electronics coupled to the one or more sensors, the electronics configured to calculate an approximation for the unknown density ($\rho_f$) based upon sensed values of whether ones of the two or more floats sink or float within the production fluid. Element 2: wherein each of the two or more floats is located in a single float chamber. Element 3: wherein each of the two or more floats is located in a separate float chamber. Element 4: wherein the one or more sensors are one or more non-contact proximity sensors. Element 5: wherein the one or more sensors are one or more contact proximity sensors. Element 6: wherein the two or more floats are three or more floats located within the one or more float chambers, the three or more floats having a density ranging from 0.6 sg to 1.2 sg, and further wherein a third of the three or more floats has a third known density ($\rho_3$) greater than the second known density ($\rho_2$). Element 7: wherein the two or more floats are four or more floats located within the one or more float chambers, the four or more floats having a density ranging from 0.7 sg to 1.1 sg, and further wherein a third of the four or more floats has a third known density ($\rho_3$) greater than the second known density ($\rho_2$), and a fourth of the four or more floats has a fourth known density ($\rho_4$) greater than the third known density ($\rho_3$). Element 8: wherein the first known density ($\rho_1$) ranges from 0.7 sg to 0.79 sg, the second known density ($\rho_2$) ranges from 0.8 sg to 0.89 sg, the third known density ($\rho_3$) ranges from 0.9 sg to 0.99 sg, and the fourth known density ($\rho_4$) ranges from 1.0 sg to 1.1 sg. Element 9: wherein the one or more sensors are one or more float sensors, and further including one or more redundant sink sensors located proximate the one or more float chambers. Element 10: further wherein the one or more float chambers and two or more floats are located within a rotating centrifuge, the rotating centrifuge configured to rotate to increase the buoyance force of the two or more floats. Element 11: wherein the rotating centrifuge is configured to rotate based upon the production fluid passing thereby. Element 12: wherein the density sensor is positioned in an annulus defined between an outer surface of the tubular and a radial outer housing. Element 13: further including a wellbore screen positioned radially about the tubular, the wellbore screen configured to receive the production fluid having the unknown density ($\rho_f$) and provide it to the annulus defined between the outer surface of the tubular and the radial outer housing. Element 14: wherein the density sensor is positioned within an interior surface of the tubular or within a sidewall of the tubular. Element 15: wherein the density sensor is a first density sensor, and further including a second density sensor positioned within the one or more production fluid flow paths, the second density sensor including: one or more second float chambers; two or more second floats located within the one or more second float chambers, the two or more second floats having a density ranging from 0.08 sg to 2.1 sg, and further wherein a first of the two or more second floats has the first known density ($\rho_1$) and a second of the two or more second floats has the second known density ($\rho_2$) greater than the first known density ($\rho_1$); and one or more second sensors located proximate the one or more second float chambers, the one or more second sensors configured to sense whether ones of the two or more second floats sink or float within the production fluid having an unknown density ($\rho_f$). Element 15: wherein the first density sensor and the second density sensor are radially offset from one another by an angle ($\Omega$) ranging from 60 degrees to 120 degrees. Element 16: wherein a first inflow control device is coupled to the tubular proximate a first production interval, and further wherein a first density sensor is coupled to the tubular proximate the first inflow control device, and further including a second inflow control device is coupled to the tubular proximate a second production interval, and further wherein a second density sensor is coupled to the tubular proximate the second inflow control device. Element 17: further including telemetry coupled to the electronics, the telemetry configured to provide the approximation for the unknown density ($\rho_f$) to a surface of the wellbore. Element 18: wherein the telemetry is wireless telemetry. Element 19: wherein the telemetry is wired telemetry. Element 20: wherein each of the two or more floats is located within the single float chamber. Element 21: wherein each of the two or more floats is located in a separate float chamber. Element 22: wherein each of the two or more floats is located in a separate caged float chamber. Element 23: wherein each of the two or more floats are fixed to an internal wire located within the tubular, each of the two or more floats configured to slide radially along the internal wire as the unknown composition of the production fluid changes. Element 24: wherein the two or more non-contact proximity sensors are eight or more non-contact proximity sensors equally radially positioned about an outer surface of the tubular. Element 25: wherein the eight or more non-contact proximity sensors are radially offset from one another by an angle ($\beta$) of less than 20 degrees. Element 26: wherein the eight or more non-contact proximity sensors are radially offset from one another by an angle ($\beta$) of less than 10 degrees. Element 27: wherein the eight or more non-contact proximity sensors are radially offset from one another by an angle ($\beta$) of less than 5 degrees. Element 28: wherein the two or more non-contact proximity sensors are twelve or more non-contact proximity sensors equally radially positioned about an outer surface of the tubular. Element 29: wherein the two or more non-contact proximity sensors are eighteen or more non-contact proximity sensors equally radially positioned about an outer surface of the tubular. Element 30: further including a third float located within the one or more float chambers, the third float having a third density ($\rho_3$) between the density of water ($\rho_w$) and a density of mud ($\rho_m$). Element 31: further including an orientation float located within the one or more float chambers, the orientation float having an orientation density ($\rho_{or}$) greater than a density of mud ($\rho_m$). Element 32: further including a third float located within the one or more float chambers, the third float having a third density ($\rho_3$) between the density of water ($\rho_w$) and a density of mud ($\rho_m$), and an orientation float located within the one or more float chambers, the orientation float having an orientation density ($\rho_{or}$) greater than the density of mud ($\rho_m$), and further wherein the first density ($\rho_1$) ranges from 0.2 sg to 0.7 sg, the second density ($\rho_2$) ranges from 0.85 sg to 0.98 sg, the third density $(\rho_3)$ ranges from 1.2 sg to 1.8 sg, and the orientation density $(\rho_{or})$ is at least 3.0 sg. Element 33: wherein the tubular is a first tubular, and further including a second tubular positioned within the first tubular, the one or more float chambers located within an annulus formed between the first tubular and the second tubular. Element 34: wherein the first tubular is wellbore casing and the second tubular is production tubing. Element 35: wherein the first tubular is the inner surface of a wellbore and the second tubular is production tubing. Element 36: wherein the first tubular is a radial outer housing and the second tubular is production tubing. Element 37: further including a wellbore screen positioned radially about the production tubing, the wellbore screen configured to receive the production fluid having the unknown composition and provide it to the annulus defined between the production tubing and the radial outer housing. Element 38: further including electronics coupled to the two or more non-contact proximity sensors, the electronics configured to calculate the approximation for the gas:oil ratio and the oil:water ratio of the production fluid having the unknown composition. Element 39: further including telemetry coupled to the electronics, the telemetry configured to provide the approximation for the gas:oil ratio and the oil:water ratio of the production fluid having the unknown composition to a surface of the wellbore. Element 40: wherein the telemetry is wireless telemetry. Element 41: wherein the telemetry is wired telemetry.

Those skilled in the art to which this application relates will appreciate that other and further additions, deletions, substitutions, and modifications may be made to the described embodiments.

What is claimed is:

1. A downhole tool, comprising:
a tubular providing one or more production fluid flow paths for a production fluid having an unknown composition, the tubular designed to reduce a flow rate of the production fluid low enough that the production fluid would separate into its components in the tubular;
one or more float chambers located within the tubular;
two or more floats located within the one or more float chambers, a first of the two or more floats having a first density $(\rho_1)$ between a density of gas $(\rho_g)$ and a density of oil $(\rho_o)$, and a second of the two or more floats having a second density $(\rho_2)$ between the density of oil $(\rho_o)$ and a density of water $(\rho_w)$, wherein the first density $(\rho1)$ ranges from 0.2 specific gravity (sg) to 0.7 specific gravity (sg), and the second density $(\rho2)$ ranges from 0.85 specific gravity (sg) to 0.98 specific gravity (sg); and
two or more non-contact proximity sensors radially positioned about an outer surface of the tubular, the two or more non-contact proximity sensors operable to sense a radial location of the two or more floats, the two or more non-contact proximity sensors configured to couple with electronics such that a gasoil ratio and oil:water ratio of the production fluid having the unknown composition may be approximated based upon the sensed radial location of the two or more floats.

2. The downhole tool as recited in claim 1, wherein at least two of the two or more floats are located within one of the one or more float chambers.

3. The downhole tool as recited in claim 1, wherein the one or more float chambers is two or more float chambers, and further wherein single ones of the two or more floats are located in respective single ones of the two or more float chambers.

4. The downhole tool as recited in claim 3, wherein the two or more float chambers are two or more caged float chambers.

5. The downhole tool as recited in claim 1, wherein each of the two or more floats are fixed to an internal wire located within the tubular, each of the two or more floats configured to slide radially along the internal wire as the unknown composition of the production fluid changes.

6. The downhole tool as recited in claim 1, wherein the two or more non-contact proximity sensors are eight or more non-contact proximity sensors equally radially positioned about the outer surface of the tubular.

7. The downhole tool as recited in claim 6, wherein the eight or more non-contact proximity sensors are radially offset from one another by an angle $(\beta)$ of less than 20 degrees.

8. The downhole tool as recited in claim 6, wherein the eight or more non-contact proximity sensors are radially offset from one another by an angle $(\beta)$ of less than 10 degrees.

9. The downhole tool as recited in claim 6, wherein the eight or more non-contact proximity sensors are radially offset from one another by an angle $(\beta)$ of less than 5 degrees.

10. The downhole tool as recited in claim 1, wherein the two or more non-contact proximity sensors are twelve or more non-contact proximity sensors equally radially positioned about the outer surface of the tubular.

11. The downhole tool as recited in claim 1, wherein the two or more non-contact proximity sensors are eighteen or more non-contact proximity sensors equally radially positioned about the outer surface of the tubular.

12. The downhole tool as recited in claim 1, further including a third float located within the one or more float chambers, the third float having a third density $(\rho_3)$ between the density of water $(\rho_w)$ and a density of mud $(\rho_m)$, wherein third density $(\rho3)$ ranges from 1.2 specific gravity (sg) to 1.8 specific gravity (sg).

13. The downhole tool as recited in claim 1, further including an orientation float located within the one or more float chambers, the orientation float having an orientation density $(\rho_{or})$ greater than a density of mud $(\rho_m)$, wherein the orientation density $(\rho or)$ is at least 3.0 specific gravity (sg).

14. The downhole tool as recited in claim 1, further including a third float located within the one or more float chambers, the third float having a third density $(\rho_3)$ between the density of water $(\rho_w)$ and a density of mud $(\rho_m)$, and an orientation float located within the one or more float chambers, the orientation float having an orientation density $(\rho_{or})$ greater than the density of mud $(\rho_m)$, and further wherein the third density $(\rho_3)$ ranges from 1.2 specific gravity (sg) to 1.8 specific gravity (sg), and the orientation density $(\rho_{or})$ is at least 3.0 specific gravity (sg).

15. The downhole tool as recited in claim 1, wherein the tubular is a first tubular, and further including a second tubular positioned within the first tubular, the one or more float chambers located within an annulus formed between the first tubular and the second tubular.

16. The downhole tool as recited in claim 15, wherein the first tubular is wellbore casing and the second tubular is production tubing.

17. The downhole tool as recited in claim 15, wherein the first tubular is the inner surface of a wellbore and the second tubular is production tubing.

18. The downhole tool as recited in claim 15, wherein the first tubular is a radial outer housing and the second tubular is production tubing.

19. The downhole tool as recited in claim 18, further including a wellbore screen positioned radially about the production tubing, the wellbore screen configured to receive the production fluid having the unknown composition and provide it to the annulus defined between the production tubing and the radial outer housing.

20. The downhole tool as recited in claim 1, wherein the two or more non-contact proximity sensors are coupled to the electronics, the electronics operable to calculate the approximation for the gas:oil ratio and the oil:water ratio of the production fluid having the unknown composition.

21. A method for operating a well system, comprising:
accessing a wellbore extending through one or more subterranean formations, the wellbore having a downhole tool located therein, the downhole tool including:
a tubular positioned within the wellbore, the tubular providing one or more production fluid flow paths for a production fluid having an unknown composition, the tubular designed to reduce a flow rate of the production fluid low enough that the production fluid would separate into its components in the tubular;
one or more float chambers located within the tubular;
two or more floats located within the one or more float chambers, a first of the two or more floats having a first density ($\rho_1$) between a density of gas ($\rho_g$) and a density of oil ($\rho_o$), and a second of the two or more floats having a second density ($\rho_2$) between the density of oil ($\rho_o$) and a density of water ($\rho_w$), wherein the first density ($\rho1$) ranges from 0.2 specific gravity (sg) to 0.7 specific gravity (sg), and the second density ($\rho2$) ranges from 0.85 specific gravity (sg) to 0.98 specific gravity (sg); and
two or more non-contact proximity sensors radially positioned about an outer surface of the tubular, the two or more non-contact proximity sensors configured to sense a radial location of the two or more floats; and
calculating an approximation for a gas:oil ratio and an oil:water ratio of the production fluid having the unknown composition using electronics coupled to the two or more sensors and the sensed radial location of the two or more floats.

22. The method as recited in claim 21, further including telemetry coupled to the electronics, the telemetry configured to provide the approximation for the gas:oil ratio and the oil:water ratio of the production fluid having the unknown composition to a surface of the wellbore.

23. The method as recited in claim 22, wherein the telemetry is wireless telemetry.

24. The method as recited in claim 22, wherein the telemetry is wired telemetry.

25. The method as recited in claim 21, wherein at least two of the two or more floats are located within one of the one or more float chambers.

26. The method as recited in claim 21, wherein the one or more float chambers is two or more float chambers, and further wherein single ones of the two or more floats are located in respective single ones of the two or more float chambers.

27. The method as recited in claim 26, wherein the two or more float chambers are two or more caged float chambers.

28. The method as recited in claim 21, wherein each of the two or more floats are fixed to an internal wire located within the tubular, each of the two or more floats configured to slide radially along the internal wire as the unknown composition of the production fluid changes.

29. The method as recited in claim 21, wherein the two or more non-contact proximity sensors are eight or more non-contact proximity sensors equally radially positioned about the outer surface of the tubular.

30. The method as recited in claim 29, wherein the eight or more non-contact proximity sensors are radially offset from one another by an angle ($\beta$) of less than 20 degrees.

31. The method as recited in claim 29, wherein the eight or more non-contact proximity sensors are radially offset from one another by an angle ($\beta$) of less than 10 degrees.

32. The method as recited in claim 29, wherein the eight or more non-contact proximity sensors are radially offset from one another by an angle ($\beta$) of less than 5 degrees.

33. The method as recited in claim 21, wherein the two or more non-contact proximity sensors are twelve or more non-contact proximity sensors equally radially positioned about the outer surface of the tubular.

34. The method as recited in claim 21, wherein the two or more non-contact proximity sensors are eighteen or more non-contact proximity sensors equally radially positioned about the outer surface of the tubular.

35. The method as recited in claim 21, further including a third float located within the one or more float chambers, the third float having a third density ($\rho_3$) between the density of water ($\rho_w$) and a density of mud ($\rho_m$), wherein the third density ($\rho3$) ranges from 1.2 specific gravity (sg) to 1.8 specific gravity (sg).

36. The method as recited in claim 21, further including an orientation float located within the one or more float chambers, the orientation float having an orientation density ($\rho_{or}$) greater than a density of mud ($\rho_m$), wherein the orientation density ($\rho or$) is at least 3.0 specific gravity (sg).

37. The method as recited in claim 21, further including a third float located within the one or more float chambers, the third float having a third density ($\rho_3$) between the density of water ($\rho_w$) and a density of mud ($\rho_m$), and an orientation float located within the one or more float chambers, the orientation float having an orientation density ($\rho_{or}$) greater than the density of mud ($\rho_m$), and further wherein the third density ($\rho_3$) ranges from 1.2 specific gravity (sg) to 1.8 specific gravity (sg), and the orientation density ($\rho_{or}$) is at least 3.0 specific gravity (sg).

38. The method as recited in claim 21, wherein the tubular is a first tubular, and further including a second tubular positioned within the first tubular, the one or more float chambers located within an annulus formed between the first tubular and the second tubular.

39. The method as recited in claim 38, wherein the first tubular is wellbore casing and the second tubular is production tubing.

40. The method as recited in claim 38, wherein the first tubular is the inner surface of a wellbore and the second tubular is production tubing.

41. The method as recited in claim 38, wherein the first tubular is a radial outer housing and the second tubular is production tubing.

42. The method as recited in claim 41, further including a wellbore screen positioned radially about the production tubing, the wellbore screen configured to receive the production fluid having the unknown composition and provide it to the annulus defined between the production tubing and the radial outer housing.

* * * * *